US007328068B2

(12) United States Patent
Spinelli et al.

(10) Patent No.: US 7,328,068 B2
(45) Date of Patent: Feb. 5, 2008

(54) METHOD, SYSTEM AND DEVICE FOR TREATING DISORDERS OF THE PELVIC FLOOR BY MEANS OF ELECTRICAL STIMULATION OF THE PUDENDAL AND ASSOCIATED NERVES, AND THE OPTIONAL DELIVERY OF DRUGS IN ASSOCIATION THEREWITH

(75) Inventors: Michele Spinelli, Milan (IT); Sylvia Malaguti, Castana (IT); Martin T. Gerber, Maple Grove, MN (US); Gianluca Giardiello, Milan (IT)

(73) Assignee: Medtronic, Inc., Minneapolis, MN (US)

( * ) Notice: Subject to any disclaimer, the term of this patent is extended or adjusted under 35 U.S.C. 154(b) by 368 days.

(21) Appl. No.: 10/723,316

(22) Filed: Nov. 26, 2003

(65) Prior Publication Data
US 2005/0113877 A1 May 26, 2005

(51) Int. Cl.
*A61N 1/00* (2006.01)
(52) U.S. Cl. ....................................................... 607/39
(58) Field of Classification Search ............ 607/39–41, 607/133, 138, 46
See application file for complete search history.

(56) References Cited
U.S. PATENT DOCUMENTS

| 3,902,501 A | 9/1975 | Citron et al. |
| 4,106,512 A | 8/1978 | Bisping |
| 4,406,288 A | 9/1983 | Horwinski et al. |
| 4,476,868 A | 10/1984 | Thompson |
| 4,566,063 A | 1/1986 | Zolnowsky et al. |

(Continued)

FOREIGN PATENT DOCUMENTS

EP 0 245 547 11/1987

(Continued)

OTHER PUBLICATIONS

"Neural Stimulation as a method of controlling prostatitis symptoms" (Chalfin), disclosed in 1999 Selected Abstracts from the American Urological Association annual meeting.*

(Continued)

*Primary Examiner*—George Manuel
(74) *Attorney, Agent, or Firm*—Shumaker & Sieffect, P.A

(57) ABSTRACT

Described are implantable devices and methods for treating various disorders of the pelvic floor by means of electrical stimulation of the pudendal or other nerves, and optional means for delivering drugs in association therewith. A method of precisely positioning and implanting a medical electrical lead so as to provide optimal stimulation of the pudendal nerve or a portion thereof is also described. Placement of a stimulation lead next to or on the pudendal nerve may be performed using conventional prior art techniques through gross anatomical positioning, but usually does not result in truly optimal lead placement. One method of the present invention utilizes neurophysiological monitoring to assess the evoked responses of the pudendal nerve, and thereby provide a method for determining the optimal stimulation site. Additionally, one or more electrical stimulation signals are applied, and optionally one or more drugs are infused, injected or otherwise administered, to appropriate portions of a patient's pelvic floor and pudendal nerve or portions thereof in an amount and manner effective to treat a number of disorders, including, but not limited to, urinary and/or fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia.

28 Claims, 19 Drawing Sheets

U.S. PATENT DOCUMENTS

| | | | |
|---|---|---|---|
| 4,607,639 A | 8/1986 | Tanagho et al. | |
| 4,692,147 A | 9/1987 | Duggan | |
| 4,739,764 A | 4/1988 | Lue et al. | |
| 4,771,779 A | 9/1988 | Tanagho et al. | |
| 4,881,526 A | 11/1989 | Johnson et al. | |
| 4,909,263 A | 3/1990 | Norris | |
| 4,987,897 A | 1/1991 | Funke | |
| 4,994,019 A | 2/1991 | Fernandez et al. | |
| 5,083,908 A | 1/1992 | Gagnebin et al. | |
| 5,199,428 A | 4/1993 | Obel et al. | |
| 5,207,218 A | 5/1993 | Carpentier et al. | |
| 5,300,107 A | 4/1994 | Stokes et al. | |
| 5,312,453 A | 5/1994 | Shelton et al. | |
| 5,330,507 A | 7/1994 | Schwartz | |
| 5,382,236 A | 1/1995 | Otto et al. | |
| 5,417,719 A | 5/1995 | Hull et al. | |
| 5,425,751 A | 6/1995 | Baeten et al. | |
| 5,454,840 A * | 10/1995 | Krakovsky et al. | 607/39 |
| 5,474,552 A | 12/1995 | Palti | |
| 5,480,656 A | 1/1996 | Okada et al. | |
| 5,501,703 A | 3/1996 | Holsheimer et al. | |
| 5,509,888 A | 4/1996 | Miller | |
| 5,540,730 A | 7/1996 | Terry, Jr. et al. | |
| 5,551,849 A | 9/1996 | Christiansen | |
| 5,562,717 A | 10/1996 | Tippey et al. | |
| 5,609,575 A | 3/1997 | Larson et al. | |
| 5,639,275 A | 6/1997 | Baetge et al. | |
| 5,643,330 A | 7/1997 | Holsheimer et al. | |
| 5,683,432 A | 11/1997 | Goedeke et al. | |
| 5,707,642 A | 1/1998 | Yue | |
| 5,733,313 A | 3/1998 | Barreras, Sr. et al. | |
| 5,800,465 A | 9/1998 | Thompson et al. | |
| 5,876,425 A | 3/1999 | Gord et al. | |
| 5,957,958 A | 9/1999 | Schulman et al. | |
| 5,984,854 A | 11/1999 | Ishikawa et al. | |
| 6,002,964 A * | 12/1999 | Feler et al. | 607/46 |
| 6,015,393 A | 1/2000 | Hovland et al. | |
| 6,055,456 A * | 4/2000 | Gerber | 607/117 |
| 6,185,452 B1 | 2/2001 | Schulman et al. | |
| 6,208,894 B1 | 3/2001 | Schulman et al. | |
| 6,210,368 B1 | 4/2001 | Rogers | |
| 6,238,423 B1 * | 5/2001 | Bardy | 607/40 |
| 6,263,246 B1 | 7/2001 | Goedeke et al. | |
| 6,283,949 B1 | 9/2001 | Roorda | |
| 6,322,330 B1 | 11/2001 | Thomas | |
| 6,358,202 B1 | 3/2002 | Arent | |
| 6,366,814 B1 | 4/2002 | Boveja et al. | |
| 6,421,566 B1 | 7/2002 | Holsheimer | |
| 6,449,512 B1 * | 9/2002 | Boveja | 607/41 |
| 6,458,118 B1 | 10/2002 | Lent et al. | |
| 6,464,670 B1 | 10/2002 | Mulholland | |
| 6,471,645 B1 | 10/2002 | Warkentin et al. | |
| 6,485,464 B1 | 11/2002 | Christenson et al. | |
| 6,551,290 B1 | 4/2003 | Elsberry et al. | |
| 6,587,719 B1 | 7/2003 | Barrett et al. | |
| 6,609,025 B2 | 8/2003 | Barrett et al. | |
| 6,650,943 B1 | 11/2003 | Whitehurst et al. | |
| 6,658,297 B2 | 12/2003 | Loeb | |
| 6,662,052 B1 | 12/2003 | Sarwal et al. | |
| 6,669,663 B1 | 12/2003 | Thompson | |
| 6,735,474 B1 | 5/2004 | Loeb et al. | |
| 6,773,428 B2 | 8/2004 | Zappala | |
| 6,862,479 B1 | 3/2005 | Whitehurst et al. | |
| 6,885,888 B2 | 4/2005 | Rezai | |
| 6,885,895 B1 | 4/2005 | Whitehurst et al. | |
| 6,901,287 B2 | 5/2005 | Davis et al. | |
| 6,907,293 B2 | 6/2005 | Grill et al. | |
| 6,941,171 B2 * | 9/2005 | Mann et al. | 607/39 |
| 6,990,376 B2 | 1/2006 | Tanagho et al. | |
| 2002/0055761 A1 | 5/2002 | Mann et al. | |
| 2002/0055779 A1 | 5/2002 | Andrews | |
| 2002/0082665 A1 | 6/2002 | Haller et al. | |
| 2003/0004533 A1 | 1/2003 | Dieck et al. | |
| 2003/0045919 A1 | 3/2003 | Swoyer et al. | |
| 2004/0049240 A1 | 3/2004 | Gerber et al. | |
| 2004/0193228 A1 | 9/2004 | Gerber | |
| 2005/0010259 A1 | 1/2005 | Gerber | |
| 2005/0010260 A1 | 1/2005 | Gerber | |
| 2005/0015117 A1 | 1/2005 | Gerber | |
| 2005/0020970 A1 | 1/2005 | Gerber | |
| 2005/0021008 A1 | 1/2005 | Gerber | |
| 2005/0033373 A1 | 2/2005 | Gerber | |
| 2005/0033374 A1 | 2/2005 | Gerber | |
| 2005/0070969 A1 | 3/2005 | Gerber | |
| 2005/0113877 A1 | 5/2005 | Spinelli et al. | |
| 2005/0113878 A1 | 5/2005 | Gerber | |
| 2005/0209652 A1 * | 9/2005 | Whitehurst et al. | 607/39 |
| 2005/0228451 A1 | 10/2005 | Jaax et al. | |
| 2005/0240229 A1 | 10/2005 | Whitehurst et al. | |
| 2005/0261746 A1 * | 11/2005 | Gross et al. | 607/41 |
| 2006/0122659 A9 | 6/2006 | Gerber | |

FOREIGN PATENT DOCUMENTS

| | | |
|---|---|---|
| WO | WO 02/078592 | 10/2002 |

OTHER PUBLICATIONS

Juenemann et al., "Clinical Significance of Sacral and Pudendal Nerve Anatomy," The Journal of Urology, vol. 139, pp. 74-80 (Jan. 1988).

Schmidt, Richard A., "Technique of Pudendal Nerve Localization for Block or Stimulation," The Journal of Urology, vol. 142, pp. 1528-1531 (Dec. 1989).

Medtronic Instruction for Use Manual, "Interstim® Therapy," Model 3080, 3092, 3886 and 3966 (32 pages) Jul. 18, 2005.

Medtronic Instruction for Use Manual, "Interstim®," Model 3080, 3092, 3886 and 3966 (36 pages) Oct. 24, 2005.

Medtronic Instruction for Use Manual, "Pisces Quad®, Compact® and Pisces Quad Plus®," Model 3487A, 3887 and 3888 (16 pages) Jan. 22, 2004.

Medtronic Instruction for Use Manual, "Interstim®," Model 4350 (40 pages) 2005.

Medtronic Instruction for Use Manual, "Interstim® Therapy," Model 3058 and 3023 (32 pages) May 5, 2006.

Medtronic Instruction for Use Manual, "Itrel® 3," Model 7425 (78 pages) Jul. 12, 2005.

Medtronic Instruction for Use Manual, "Synergy™ and Synergy Versitrel™," Model 7427 and 7427V (96 pages) Oct. 30, 2003.

Medtronic Instruction for Use Manual, Model 7424 (57 pages) Sep. 1993.

U.S. Appl. No. 09/713,598, filed Nov. 15, 2000, entitled "Minimally Invasive Apparatus for Implanting a Sacral Stimulation Lead."

Chalfin, S.A., "Neural Stimulation as a Method of Controlling Prostatitis Symptoms," disclosed in 1999 Selected Abstracts from American Urological Association Annual Meeting, 2 pages.

* cited by examiner

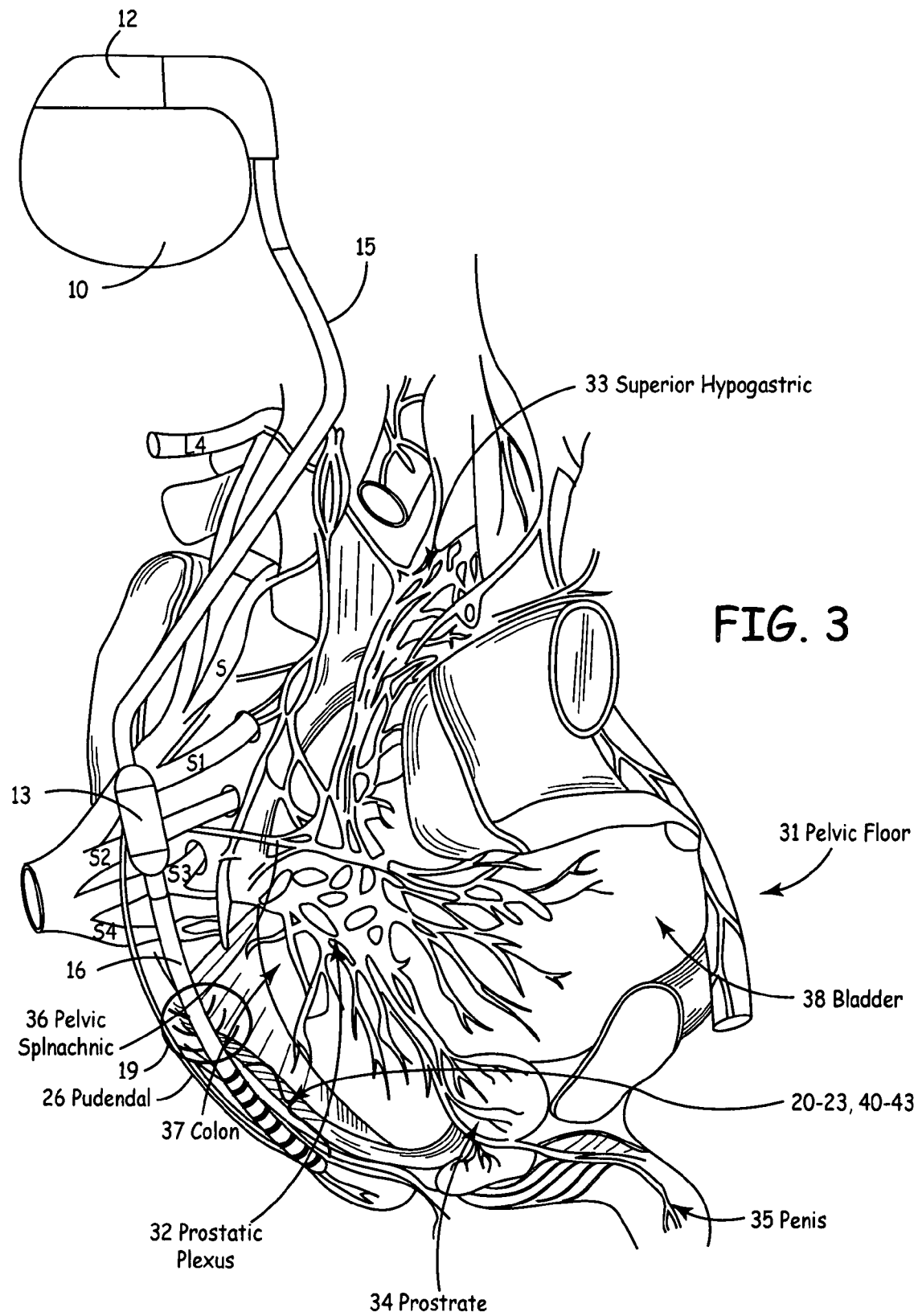

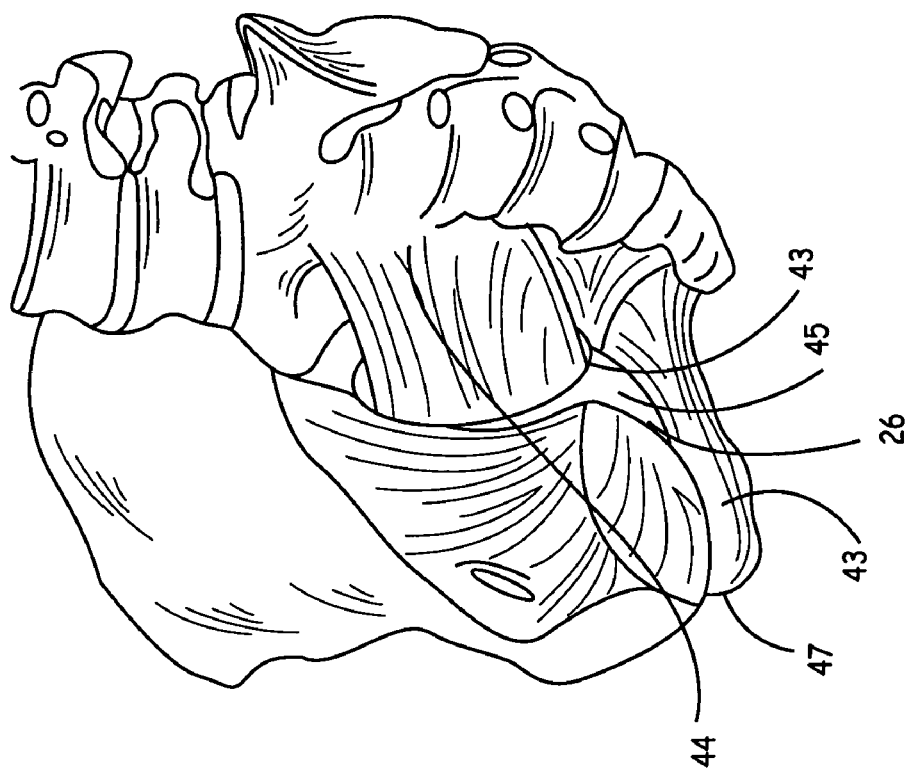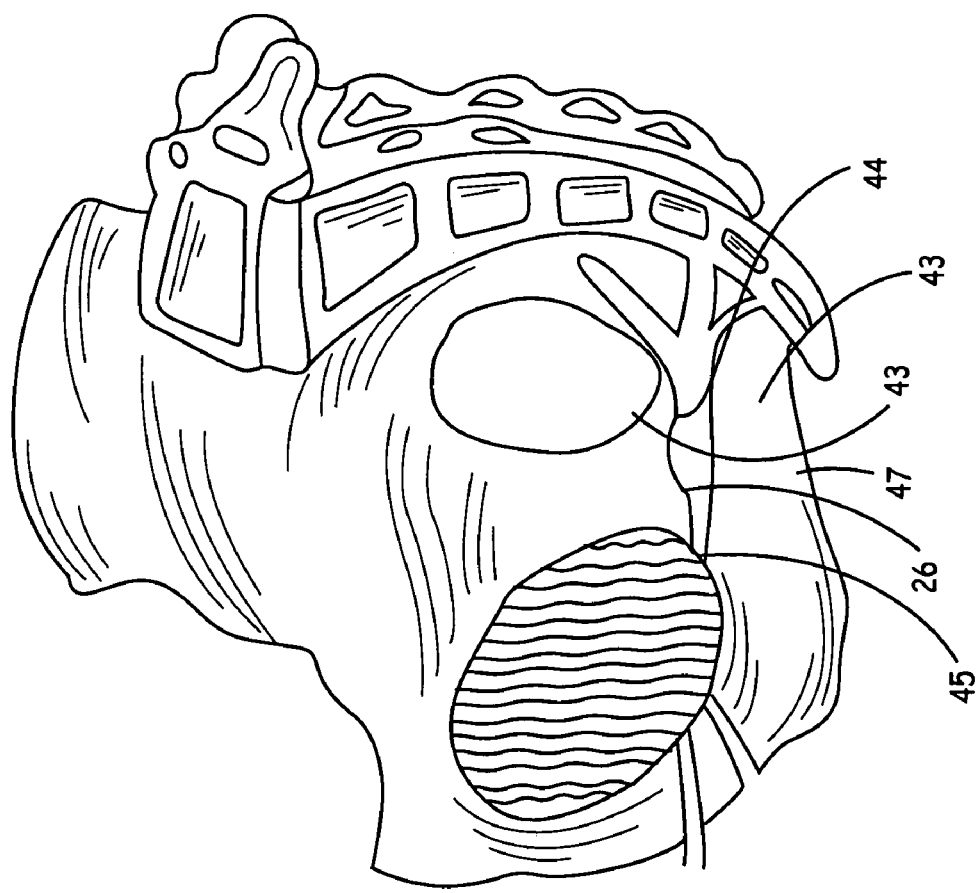
FIG. 5

METHOD, SYSTEM AND DEVICE FOR TREATING DISORDERS OF THE PELVIC FLOOR BY MEANS OF ELECTRICAL STIMULATION OF THE PUDENDAL AND ASSOCIATED NERVES, AND THE OPTIONAL DELIVERY OF DRUGS IN ASSOCIATION THEREWITH

RELATED APPLICATIONS

This application claims priority from U.S. Provisional Application No. 60/459,077, filed Mar. 31, 2003, entitled "Method, System and Device for Treating Disorders of the Pelvic Floor by Means of Electrical Stimulation of the Pudenal and Associated Nerves, and the Optional Delivery of Drugs in Association Therewith" to Spinelli et al., which is hereby incorporated by reference in its entirety.

FIELD OF THE INVENTION

This invention relates to implantable devices and methods for treating urinary and fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia utilizing electrical stimulation and, optionally, the delivery of drugs.

BACKGROUND

This disclosure relates to a method to locate the pudendal nerve, to determine optimum stimulation location and to acutely determine if the patient is responsive to stimulation.

The medical device industry produces a wide variety of electronic and mechanical devices for treating patient medical conditions. Depending upon the medical condition, medical devices can be surgically implanted or connected externally to a patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Conditions that medical devices can effectively treat include pelvic floor disorders.

Pelvic floor disorders adversely affect the health and quality of life of millions of people. Pelvic floor disorders include urinary control disorders such as urge incontinency, urge frequency, voiding efficiency, fecal control disorders, sexual dysfunction, and pelvic pain. Individuals with urinary control disorders often face debilitating challenges in their everyday lives. These individuals can be preoccupied with trips to the bathroom, fears of embarrassment, and sleepless nights. Some suffers become so anxious they become isolated and depressed. Pelvic floor disorders can be treated with a variety of therapeutic options such as behavior modification including biofeedback, pharmacological treatment, mechanical intervention such as self-catheterization, physical appliances such as diapers, and surgical intervention. Surgical treatments are the most invasive and are often considered after other therapies have proven ineffective.

Urinary incontinence, the inability to control the passage of urine, is a relatively common problem. Although there are a variety of different types of urinary incontinence, stress incontinence, urge incontinence and urinary retention are the most common.

Stress incontinence is described by the patient as the unacceptable passage of urine under the stress of increased abdominal pressure. This increased pressure typically results from coughing, sneezing, and Valsalva. Stress incontinence is manifested urologically by normal cystometry, obtuse urethral vesicular angle, abnormally low urethral pressures and a physiologically short urethral length. This disorder is most common in multiparous, post-menopausal females. Physiologically, stress incontinence is a disorder of the volitional muscular control of the urethral resistance to the flow of urine. Laxity and partial denervation of the pelvic musculature is the chief abnormality.

Urge incontinence is described as the involuntary passage of urine with a concomitant sense of urgency. Systometry indicates detrusor (bladder wall muscle) contractions with low bladder filling pressures and volumes. These bladder contractions may not be inhibited in the presence of voluntary EMG signals from the sphincter, indicating reduction or loss of the pudendal-parasympathetic inhibitory reflex. Unsolicited, premature bladder contraction may result from mucosal irritation of varied etiology. These premature contractions of the bladder may also be the result of an abnormally high gain in the detrusor contractile reflex due to the loss of inhibitory control with an upper-motor-neuron lesion.

Urinary retention is characterized by the inability of a patient to spontaneously and controllably urinate or void. Catheterization of the urethra is provided to many patients suffering from urinary retention, which is often a painful and somewhat lengthy procedure having the added risk of causing infection.

Constipation is a life-disturbing problem that afflicts millions of Americans, from the very young to the elderly. Although relatively rare among the young, it is a very common problem in middle age, and is a nearly ubiquitous problem in the elderly.

Chronic constipation is a major problem for many individuals, and frequently causes extreme discomfort to the afflicted. Such discomfort may be a major obstacle to leading a normal life, and may consume an enormous amount of the afflicted person's energy and time.

Besides causing severe discomfort, chronic constipation may also be harmful to the patient. For example, chronic constipation may result in an intestinal obstruction that may cause the patient great pain; or that may even cause the patient's death, unless surgically corrected. Chronic constipation may also prevent the patient from receiving the benefit of certain needed prescription medications, because the medications may have undesirable side effects on an already constipated gut.

Conventional therapies for chronic constipation are often distasteful and unpleasant, at best, since they may involve such treatments as the repeated consumption of large quantities of laxatives such as milk of magnesia, the repetitive use of enemas, or both. Repeatedly consuming large quantities of laxatives may be harmful to the patient, since they may result in dehydration or even renal failure. The repetitive use of enemas may be harmful since they may irritate or physically harm the treated portion of the patient's gut.

Chronic constipation is usually thought of in association with problems of the large intestine. However, other parts of the patient's gut may also exhibit chronic constipation-like problems, such as the esophagus, the stomach, and less frequently, the small intestine. Such problems may include depressed motility of the esophagus, stomach and/or small intestine. For simplicity, chronic constipation, or chronic constipation-like problems, of any portion of the patient's gut from the esophagus to the anus will be referred to hereafter as simply "constipation".

The prostate is a glandular and fibromuscular organ in the male, which lies immediately below the bladder and surrounds the urethra. Prostatitis, the third leading disease of the prostate, is a common urologic condition that many clinicians find difficult to treat effectively.

The main symptom of chronic prostatitis (category III) is pain, followed by variable voiding (urgency/frequency) and erectile or sexual dysfunction. Patients have symptoms such as painful ejaculation or pain in the penis, testicles, or scrotum; low back, rectal or perineal pain; pain along the inner aspects of the thighs; irritative or obstructive urinary symptoms; and decreased libido or impotence. As a rule, chronic non-bacterial prostatitis patients do not have recurrent urinary tract infections.

Chronic prostatitis is a major male health issue. The average urologist in the U.S. sees 173 prostatitis patients per year, of which one-third are newly diagnosed. The prevalence of prostatitis in the general male population is estimated to be 5-8.8%, and it has been estimated that about 2 million office visits per year are related to prostatitis. Self-reported history of prostatitis is as prevalent as 16%. Patients with chronic prostatitis experience a negative impact on quality of life comparable to patients with unstable angina, recent myocardial infarction, or active Crohn's disease. The average age of the prostatitis population is estimated at 50 years, is the most common urologic diagnosis in men under 50 years old and the third most common in men over 50 years old. The most common classification of prostatitis is chronic prostatitis/chronic pelvic pain syndrome (category III), which may include as many as 90% of all patients who meet the criteria of the condition. Despite the widespread prevalence of prostatitis, the diagnosis of chronic prostatitis represents a particular challenge since its diagnosis is often based on exclusion.

Prostatitis remains poorly understood despite its prevalence because it encompasses multiple diverse disorders that cause symptoms related to the prostate gland. The etiology of acute and chronic bacterial prostatitis is clearly defined, and is a result of pathogenic bacteria that may cause systemic symptoms or urinary tract infections. On the other hand, chronic prostatitis/chronic pelvic pain syndrome does not have a clearly defined etiology, and there are many theories about the cause of this disease.

Perhaps the most encompassing theory of chronic non-bacterial prostatitis involves a multifactorial mechanism initiated by a stimulus such as infection or trauma. An interrelated cascade of events may follow, including physical, chemical, immunologic or neurogenic components, resulting in a local response of inflammation and/or neurogenic injury.

In the absence of consistent or clear etiologies for chronic prostatitis/chronic pelvic pain syndrome, improvement in quality of life and a reduction in symptoms are the usual goals of therapy. The most common treatment of chronic prostatitis includes pharmacologic treatments (antibiotics, anti-inflammatory agents, alpha blockers, anti-spasmodics, analgesics, allopurinol, and muscle relaxants). Alpha blockers have successfully treated symptoms, although adverse event rates have been high. Muscle relaxants have shown significant improvement in small studies for category IIIB patients with sphincter dyssynergia or muscle spasm. Anti-inflammatory agents, such as pentosan polysulfate, have proven successful for approximately 40% of patients with category IIIA prostatitis.

Phytotherapeutic agents have demonstrated improvements in small studies for pain and irritative voiding. Other treatments include physiotherapy (such as biofeedback and pelvic muscle exercises) and various modalities of invasive and minimally invasive procedures (e.g., transurethral microwave therapy, transurethral incision of the bladder neck, hydrodistensions, acupuncture, electroneuromodulation, balloon dilation, YAG laser therapy and heat therapy). Repetitive prostatic massage is a popular treatment method due to the failure of consistent standard medical therapy to treat the condition. Lifestyle changes, such as meditation, discontinuation of bike riding, sitz-baths, dietary changes, and chiropractic therapy, are often utilized.

As a result of unknown etiology, unsure diagnosis, and treatment options that are often myriad and ineffective, chronic prostatitis is a "diagnosis of exclusion" and has a poor record of treatment success. Accordingly, the present invention is intended to provide solutions to the foregoing problems through improved and more effective methods of treating pain and other symptoms associated with chronic prostatitis, prostatalgia and prostatodynia.

Sexual dysfunction comprises a broad range of maladies, including erectile dysfunction, orgasmic dysfunction, premature ejaculation, and lack of lubrication. Sexual dysfunctions plague both women and men, and may be life-long or acquired. To treat impotence (also called erectile dysfunction) it is known to implant electrical conductors to the surface of the pelvic splanchnic nerve. Stimulation of this nerve with low voltage electrical pulses is believed to cause arterioles dilation and initiate erection. Also, it is known that implantation of an electrode on the cavernous nerves of a male, adjacent to his prostate gland, may also achieve penile erection. Further, other electrical impulse devices exist that are not implanted but instead applied topically to the coccyx region to promote sexual excitation. Impotence, however, should not be confused with orgasmic dysfunction where satisfactory erection may be obtained but there is an absence of orgasm.

Current treatment of orgasmic dysfunction concentrates on the psychological components of the disorder rather than the physiological components. Orgasmic dysfunction is a physical malady that results in marked distress and interpersonal difficulty. The physical disorder causes psychological performance anxiety and pressure. Sexual desire and frequency usually decline. The patient's intimate relationships ultimately suffer from resentment and conflict. There is anecdotal evidence of patients who have experienced mild sensation of the genitalia while undergoing spinal cord stimulation for pain relief.

Spinal cord stimulation, on the other hand, has been used as a treatment for chronic painful conditions for approximately thirty years. Commonly, spinal cord stimulation is used to alleviate pain after failed surgery, pain due to neuropathies, or pain due to inadequate blood flow. Neurostimulation systems have been found to relieve chronic, intractable pain in the limbs or trunk.

The basic concept of neurostimulation as it relates to pain relief involves the substitution of sensations that reach the thalamus of the brain. Rather than a pain message, the spinal cord stimulation closes the gate in the spinal cord and replaces the pain sensation with a tingling sensation. Electrodes are positioned effectively to create parathesia in the painful area. Parathesia refers to a change in sensation in an area of the body. Usually parathesia is used to show change in neurologic function caused by damage to a nerve or nerves. Parathesia is usually not an absence of sensation, but a decrease or alteration of sensation. Patients have described parathesia as a "buzzing sensation."

Parathesia is accomplished through the implantation of stimulating electrodes within the spinal canal. The electrodes are inserted between the vertebrae in parallel with the spinal cord. Low-voltage electrical stimulation is precisely applied to the spinal cord. Through direct stimulation of the dorsal column or the targeted peripheral nerve, the sensation of pain is replaced by a more pleasant "tingling" sensation. The sensation can be adjusted in terms of amplitude to control intensity, pulse width to control duration and frequency. Further, the neurostimulation system is implantable in its entirety. Medtronic Neurological, a division of Medtronic, Inc. of Minneapolis, Minn. sells a neurostimulator system used for pain relief. The device has been approved by the Federal Drug Administration for implantation in the spinal cord to effectively alleviate pain.

One surgical technique to treat urinary control disorders is implantable InterStim® therapy, available from Medtronic, Inc., which applies mild electrical stimulation to the sacral nerves in the lower region of the spine to influence behavior of structures such as the bladder, sphincter and pelvic floor muscles. Generally, implantation of InterStim therapy involves surgically implanting a stimulation lead near the sacral nerves. The stimulation lead is a very small, insulated electrical conductor with electrical stimulation contacts on the distal end placed near the sacral nerves and an electrical connector on the opposite proximal end of the lead. The lead electrical connector is typically connected to a small extension, and the extension is connected to a small neurostimulator that operates similar to a cardiac pacemaker by delivering occasional small electrical pulses that sometimes create a tingling sensation felt by the patient. The stimulation lead, lead extension, and neurostimulator are all implanted in the patient in a manner that is typically not perceptible by others. InterStim therapy can improve the condition of a pelvic floor disorder patient and allow the patient to lead a full life. Also, InterStim therapy is nondestructive and reversible.

Today, stimulation of the sacral nerve is commonly done for the treatment of voiding dysfunction. Although the majority of patients with sacral nerve stimulation obtain satisfactory relief of their voiding dysfunction, some patients do not experience an improvement in symptoms or see annoying side effects that prohibit them from using the therapy.

Electrical stimulation delivered by an intravaginal or a perineal surface electrode has been shown to inhibit premature and inappropriate detrusor contractions. The mechanism for this effect appears to derive from the stimulation of pudendal nerve afferents (sensory receptors or sensory nerve fibers). Input into the pudendal afferent system inhibits a parasympathetic reflex loop consisting of bladder wall afferents (sensory) and efferents (motor). This parasympathetic loop normally senses a distension of the bladder via the afferent limb and responds by sending an efferent signal to contract the bladder. Although this stimulation has shown therapeutic effects, electrode placement and on-going stimulation does not lend itself toward chronic stimulation.

Stimulation of the pudendal nerve as an alternative to sacral nerve stimulation has been proposed previously. The invasiveness of surgical procedures made stimulation of the pudendal nerve impractical, however.

Some prior art publications relating to various embodiments of the present invention are listed in Table 1 below.

Table 1: Prior Art Publications

Juenemann et al., "Clinical Significance of Sacral and Pudendal Nerve Anatomy,"The Journal of Urology, Vol. 139, pp. 74-80 (January, 1988).

Schmidt, Richard A., "Technique of Pudendal Nerve Localization for Block or Stimulation," The Journal of Urology, Vol. 142(December, 1989).

U.S. Pat. No. 4,406,288 to Cash for "Bladder Control Device and Method"

U.S. Pat. No. 4,607,639 to Tanagho et al. for "Method and System for Controlling Bladder Evacuation."

U.S. Pat. No. 4,771,779 to Tanagho et al. for "System for Controlling Bladder Evacuation."

U.S. Pat. No. 4,739,764 to Lue et al. for "Method for Stimulating Pelvic Floor Muscles for Regulating Pelvic Viscera."

U.S. Pat. No. 4,881,526 to Johnson et al. for "Intravaginal Electrode and Stimulation System for Controlling Female Urinary Incontinence"

U.S. Pat. No. 5,425,751 to Baeten et al. for "Method and Apparatus for Optimum Positioning of a Muscle Stimulating Implant"

U.S. Pat. No. 5,984,854 to Ishikawa et al. for "Method for Treating Urinary Incontinence and Apparatus Therefor"

U.S. Pat. No. 6,055,456 to Gerber for "Single and Multi-Polar Implantable Lead for Sacral Nerve Stimulation"

U.S. Pat. No. 6,366,814 to Boveja. for "Electrical Stimulation Adjunct (Add-On) Therapy for Urinary Incontinence and Urological Disorders Using an External Stimulator"

U.S. Pat. No. 6,449,512 to Boveja. for "Apparatus and Method for Treatment of Urological Disorders Using Programmerless Implantable Pulse Generator System"

U.S. patent application Publication No. 2002/0055761 to Mann et al. for "Implantable Stimulator Systems and Methods for Treatment of Incontinence and Pain"

U.S. patent application Publication No. 2002/0055779 to Andrews for "Neural Prosthesis"

PCT Patent Application WO 02/078592 to Grill et al. for "Systems and Methods for Selectively Stimulating Components In, On or Near the Pudendal Nerve or Its Branches to Achieve Selective Physiologic Responses"

European Patent Application No. 0 245 547 to Tanagho et al. for "Electronic Control System for Controlling Pelvic Viscera via Neuro-Electrical Stimulation."

All patents and technical papers listed in Table 1 hereinabove are hereby incorporated by reference herein, each in its respective entirety. As those of ordinary skill in the art will appreciate readily upon reading the Summary of the Invention, Detailed Description of the Preferred Embodiments and Claims set forth below, at least some of the devices and methods disclosed in the patents and publications of Table 1 may be modified advantageously in accordance with the teachings of the present invention. The foregoing and other objects, features and advantages, which will now become more readily apparent by referring to the following specification, drawings and claims, are provided by the various embodiments of the present invention.

For the foregoing reasons, there exists an unfulfilled need in the art for a method to locate the pudendal nerve, to determine optimum electrical stimulation locations and to determine acutely whether a patient respond to electrical stimulation therapy.

SUMMARY OF THE INVENTION

Electrical stimulation of the pudendal nerve has been discovered to provide a means of more directly or effectively stimulating portions of the pelvic floor than has been possible heretofore employing conventional sacral nerve electrical stimulation techniques. It is believed that the pudendal nerve more directly innervates the pelvic floor and portions thereof than does stimulation of a sacral nerve. It has been discovered that electrical stimulation of the pudendal nerve or portions thereof provides beneficial effects and therapy for various disorders of the pelvic floor over a wider anatomical region than merely the pudendal nerve or portion thereof which is being stimulated, or than may be attained through conventional sacral nerve stimulation. Because the present invention provides for more targeted electrical stimulation of the pelvic floor or portions thereof, at least some of the undesirable side effects of sacral nerve stimulation may be avoided or minimized.

One embodiment of the present invention relates to a method of precisely positioning and implanting a medical electrical lead so as to provide optimal stimulation of the pudendal nerve or a portion thereof. Placement of a stimulation lead next to or on the pudendal nerve may be performed using conventional prior art techniques through gross anatomical positioning, but usually does not result in truly optimal lead placement. One method of the present invention utilizes neurophysiological monitoring to assess the evoked responses of the pudendal nerve, and thereby provide a method for determining the optimal stimulation site.

One or more electrical stimulation signals are applied, and optionally one or more drugs are infused, injected or otherwise administered, to appropriate portions of a patient's pelvic floor and pudendal nerve or portions thereof in an amount and manner effective to treat a number of disorders, including, but not limited to, urinary and/or fecal voiding dysfunctions such as constipation, incontinence disorders such as urge frequency and urinary retention disorders, sexual dysfunctions such as orgasmic and erectile dysfunction, pelvic pain, prostatitis, prostatalgia and prostatodynia.

The at least one electrical stimulation signal is applied by an IMD that has at least one medical electrical lead positionable, secured or attached to or in a patient's pelvic floor and in proximity to a pudendal nerve or portion thereof. Each such lead carries at least one electrode, and preferably at least two electrodes, positionable or attachable for contact with or in proximity to the patient's pudendal nerve or portion thereof.

The present invention has certain objects. That is, various embodiments of the present invention provide solutions to one or more problems existing in the prior art respecting conventional treatment for pelvic pain, sexual dysfunction, prostadynia, prostatitis, prostatalgia, and/or urinary or fecal incontinence in a patient, including one or more of: (a) sequelae or side-effects resulting from the administration of pharmaceutical products; (b) the requirement to purchase expensive pharmaceutical products on an on-going basis; (c) not having the ability to terminate or change instantaneously administration of pharmaceutical therapy; (d) not having the ability to target with a great deal of precision or specificity the ailment in question using pharmaceutical products; (e) in the case of electrical stimulation, not having a well-defined or reliable method of determining stimulation electrode placement; (f) patients having chronic and essentially untreatable pain having no effective pain relief therapy available for use; (g) patients having to wear diapers, pads or other devices for containing human waste, and/or (f) conventional sacral nerve stimulation techniques being incapable of providing the desired relief or therapy in many patients.

Various embodiments of the present invention have certain advantages, including one or more of: (a) determining with a high degree of precision the optimal location for one or more stimulation electrodes in a patient; (b) with a chronic stimulation lead, providing a relatively reliable method of replicating the electrode position of a screening or temporary stimulation lead when implanting the chronic lead in a patient; (c) determining with a high degree of confidence, before or during the implantation procedure, whether electrical stimulation techniques are capable of providing the desired relief or therapy to a patient; (d) in accordance with (c), preventing unnecessary implants of electrical stimulation devices in patients; (e) targeting delivery of therapy with a high degree of specificity; (f) having the ability to change the therapy delivered on-demand or instantaneously; (g) lowering medical care costs in respect of pharmaceutical products; (h) having the potential to delivery superior therapy; (i) a patient not having to remember to take a drug daily or according to a predetermined regimen; (j) permitting stimulation lead implantation surgical procedures to be completed more quickly; (d) reducing trauma or damage to a patient's pelvic floor anatomy; and/or (e) improved physical and electrical coupling of one or more stimulation electrodes to a pertinent nerve or nerve portion.

BRIEF DESCRIPTIONS OF THE DRAWINGS

These and other objects, features and advantages of the present invention will be more readily understood from the following detailed description of the preferred embodiments thereof, when considered in conjunction with the drawings, in which like reference numerals indicate identical structures throughout the several views when appropriate. Note that the drawings are not necessarily to scale.

FIG. 1 shows one embodiment of the present invention, where INS 10 is implanted in an upper buttock position in a patient and lead 16 is implanted near or adjacent to nerve or nerve portion 8 (such as pudendal nerve 26) to thereby effect therapeutic relief;

FIG. 3 shows a simplified anatomical view of the pelvic floor of a human patient, the locations of the pudendal and associated nerves therein, and an illustrative positioning of IMD 10 and electrical stimulation lead 16 and corresponding electrodes 20-23 and/or 40-43;

FIG. 4c shows a simplified anatomical view of the locations of the pudendal nerve and its associated branches in the patient of FIG. 4a;

FIG. 5 shows further simplified anatomical views of the pelvic floor and the locations of the pudendal and associated nerves therein;

DESCRIPTION OF THE PREFERRED EMBODIMENTS

In the following description of the preferred embodiments, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense. Instead, the scope of the present invention is to be defined in accordance with the appended claims. As employed herein, the term "pudendal nerve 26" means the pudendal nerve itself, portions of the pudendal nerve, nerves neurologically connected to the pudendal nerve and in relatively close physical proximity thereto, and extensions or branches of the pudendal nerve.

Figure 1:
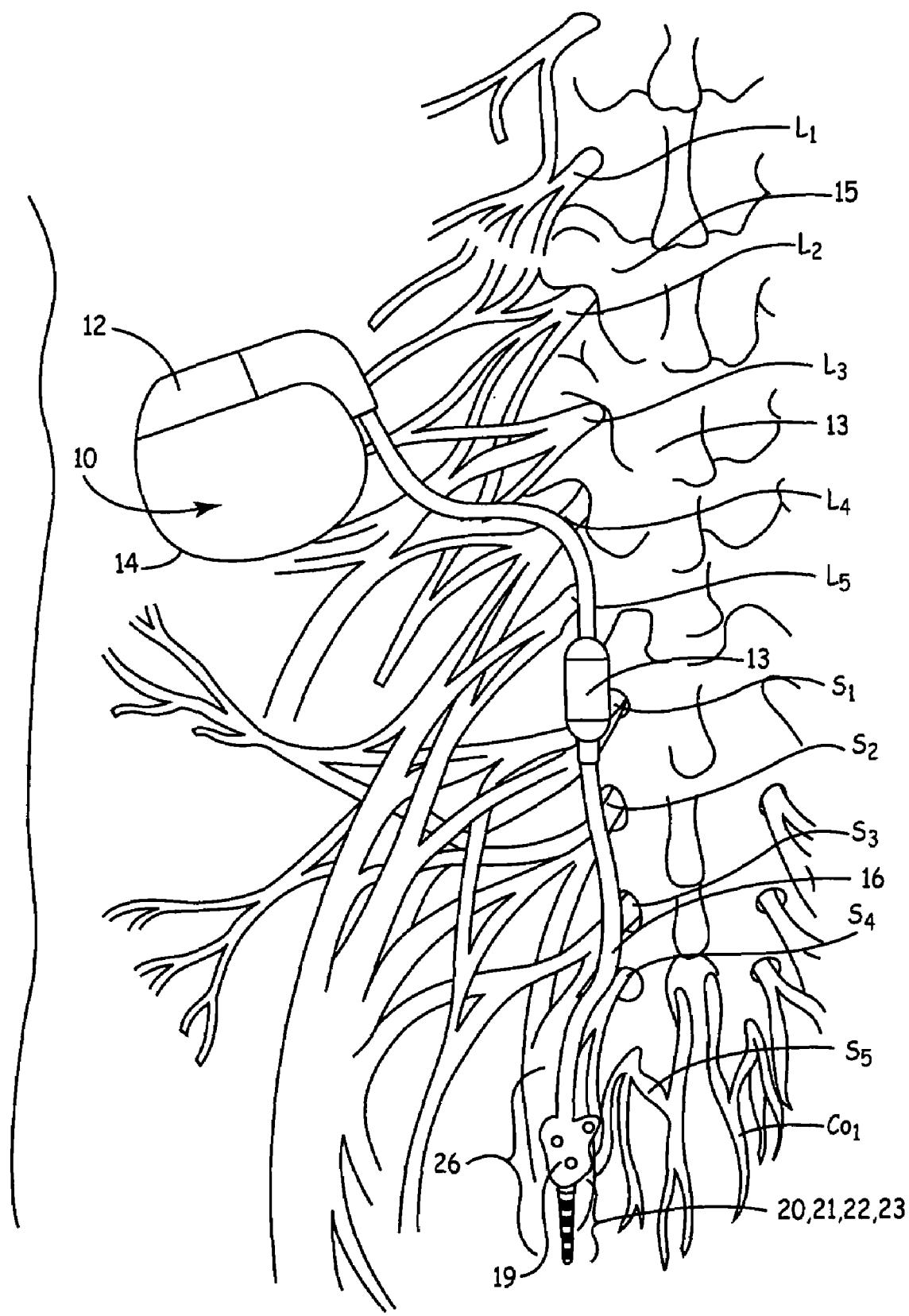

FIG. 1 shows one embodiment of the present invention, where INS 10 is an implantable electrical stimulator comprising at least one implantable medical electrical lead 16 attached to hermetically sealed enclosure 14. Enclosure 14 is preferably formed of a biocompatible material such as an appropriate metal alloy containing titanium. In FIG. 1, INS 10 is shown as being implanted in an upper buttock position in a patient and lead 16 is implanted near or adjacent to nerve or nerve portion 8 (such as pudendal nerve 26) to thereby effect therapeutic relief. Note, however, that INS 10 may be implanted in any appropriate location in the patient, such as in the abdomen or side. Relief is effected as a result of electrical stimulation signals being delivered to or near pudendal nerve 26 or nerve or nerve portion 8 by electrodes 20-23. One, two, three, four or more electrodes 20, 21, 22 and 23 may be disposed at the distal end of lead 16. FIG. 1 shows four electrodes located at the distal end of lead 16 near pudendal nerve 26. Other lead locations and electrode configurations are possible and contemplated in the present invention.

It is important to note that one or more leads such as 16 and 18 (not shown in FIG. 1) may be employed in accordance with certain embodiments of the present invention, where multiple nerve target sites or portions are to be stimulated simultaneously or sequentially and/or where such multiple target sites or portions are incapable of being stimulated, or are difficult to stimulate, using a single lead, even if the single lead contains multiple stimulation electrodes or arrays of stimulation electrodes.

In one embodiment of the present invention, Lead 16 provides electrical stimulation pulses to the desired nerve target sites or portions 8 and thereby causes paresthesia, the masking or blocking pain signals originating in or carried by a desired or target nerve or nerve portion 8 located in the vicinity of the electrode(s) thereof. Leads 16 and 18 may have unipolar electrodes disposed thereon (where enclosure 14 is employed as an indifferent electrode) or may have bipolar electrodes disposed thereon, where one or more electrodes disposed on a lead are employed as the indifferent electrode. In one embodiment of the present invention, Lead 16 extends from lead connector 13, which in turn forms an integral portion of lead extension 15 connected at its proximal end to connector header module 12.

Typically, leads 16 and 18 are tunneled subcutaneously between the location of INS 10 and the location or site of the nerve or nerve portion 8 that is to be stimulated. INS 10 is typically implanted in a subcutaneous pocket formed beneath the patient's skin according to methods well known in the art. Further details concerning various methods of implanting INS 10 and leads 16 and 18 are disclosed in the Medtronic Interstim Therapy Reference Guide published in 1999, the entirety of which is hereby incorporated by reference herein. Other methods of implanting and locating leads 16 and 18 are of course contemplated in the present invention.

Some representative examples of leads 16 and 18 include MEDTRONIC nerve stimulation lead model numbers 3080, 3086, 3092, 3487, 3966 and 4350 as described in the MEDTRONIC Instruction for Use Manuals thereof, all hereby incorporated by reference herein, each in its respective entirety. Some representative examples of INS 10 include MEDTRONIC implantable electrical stimulator model numbers 3023, 7424, 7425 and 7427 as described in the Instructions for Use Manuals thereof, all hereby incorporated by reference herein, each in its respective entirety. INS 10 may also be constructed or operate in accordance with at least some portions of the implantable stimulators disclosed in U.S. Pat. No. 5,199,428 to Obel et al., U.S. Pat. No. 5,207,218 to Carpentier et al. or U.S. Pat. No. 5,330,507 to Schwartz, all of which are hereby incorporated by reference herein, each in its respective entirety.

U.S. patent application Ser. No. 10/004,732 entitled "Implantable Medical Electrical Stimulation Lead Fixation Method and Apparatus" and Ser. No. 09/713,598 entitled "Minimally Invasive Apparatus for Implanting a Sacral Stimulation Lead" to Mamo et al., the respective entireties of which are hereby incorporated by reference herein, describe methods of percutaneously introducing leads 16 and 18 to a desired nerve stimulation site in a patient.

Figure 2A:
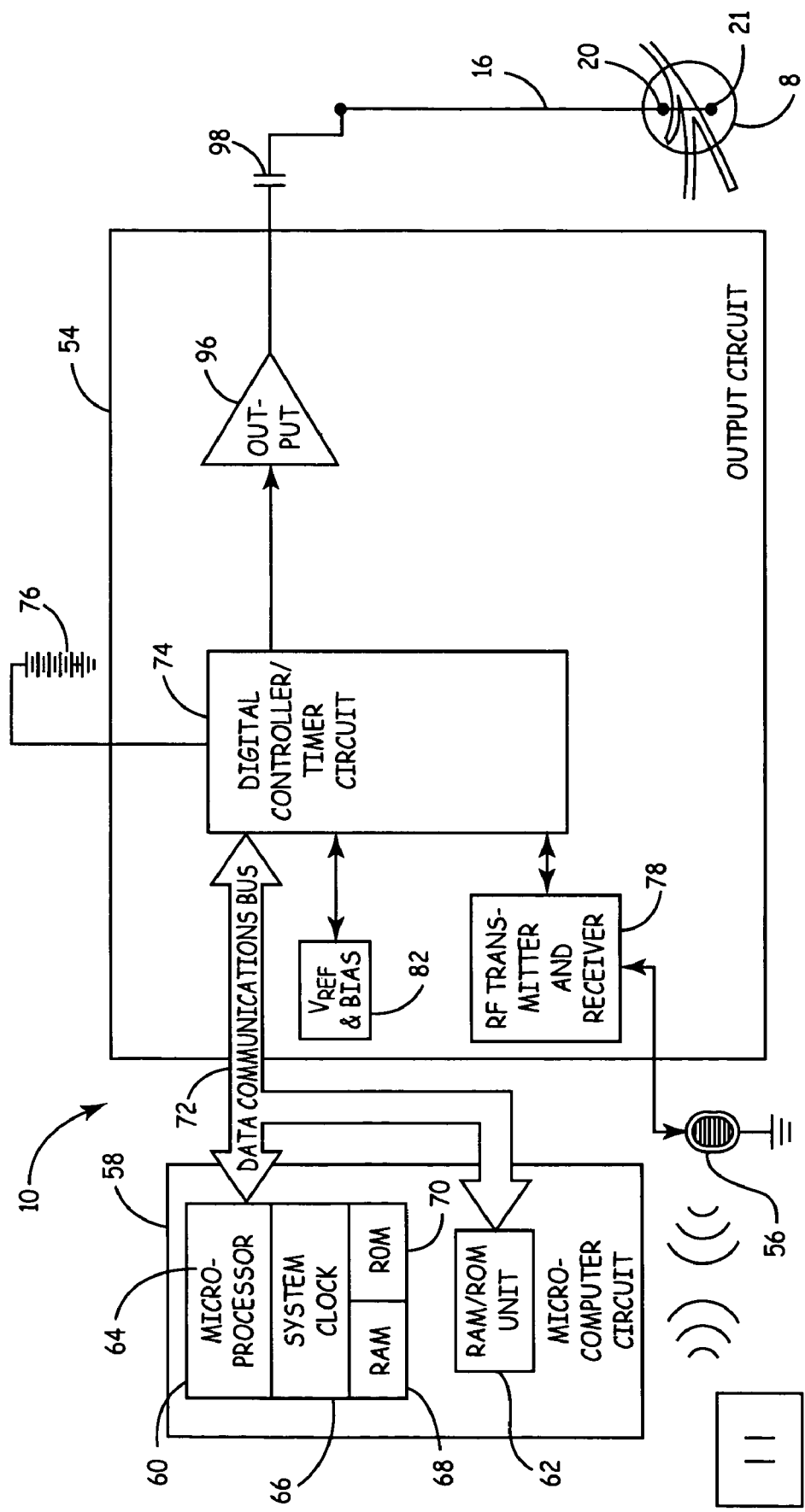
FIGS. 2a and 2b show block diagrams illustrating some of the constituent components of INS 10 in accordance with one embodiment of the present invention.
Figure 2B:
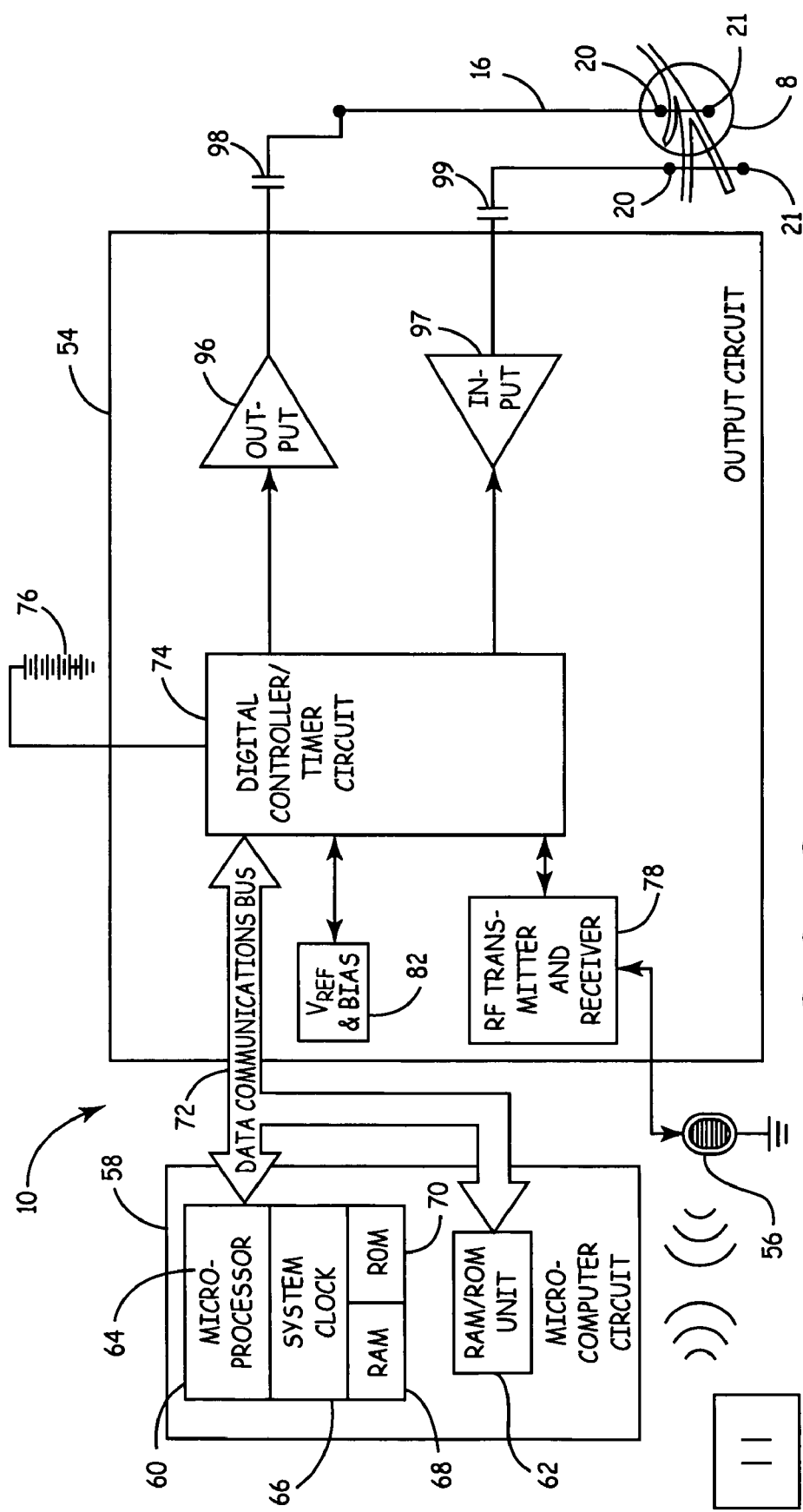

FIG. 2s shows a block diagram illustrating some of the constituent components of INS 10 in accordance with one embodiment of the present invention, where INS 10 is an implantable electrical stimulator having a microprocessor- or controller-based architecture, and such system is an open-loop system. Other architectures of INS 10 are of course contemplated in the present invention, such as that shown in FIG. 2b (a closed loop system), or the logic or state machine architecture employed in the Medtronic Model Number 3023 INS. For the sake of convenience, INS 10 in FIG. 2a is shown with only one lead 16 connected thereto; similar circuitry and connections not shown in FIG. 2a apply generally to lead 18 and other additional leads not shown in the drawings. INS 10 in FIG. 2a is most preferably programmable by means of external programming unit 11. One such programmer is the commercially available Medtronic Model No. 7432 programmer, which is microprocessor-based and provides a series of encoded signals to INS 10, typically through a programming head which transmits or telemeters radio-frequency (RF) encoded signals to INS 10. Another suitable programmer is the commercially available Medtronic Model No. 8840 programmer, which is also microprocessor-based but features a touch control screen.

Any of a number of suitable programming and telemetry methodologies known in the art may be employed so long as the desired information is transmitted to and from the implantable electrical stimulator 10.

FIG. 2a further shows a block diagram illustrating some of the constituent components of INS 10 in accordance with one embodiment of the present invention. Lead 16 is coupled to node 50 in INS 10 through input capacitor 52. Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 2a are powered by an appropriate implantable primary (i.e., non-rechargeable) battery power source 76 or secondary (i.e., rechargeable) battery power source 76. For the sake of clarity, the coupling of battery 76 to the various components of INS 10 is not shown in the Figures. Antenna 56 is connected to microcomputer circuit 58 via digital controller/timer circuit 74 and data communication bus 72 to permit uplink/downlink telemetry through RF transmitter and receiver telemetry unit 78. By way of example, telemetry unit 78 may correspond to that disclosed in U.S. Pat. No. 4,566,063 issued to Thompson et al. It is generally preferred that the particular programming and telemetry scheme selected permit the entry and storage of electrical stimulation parameters. The specific embodiments of antenna 56 and other telemetry circuitry presented herein are shown for illustrative purposes only, and are not intended to limit the scope of the present invention.

Continuing to refer to FIG. 2a, VRF and bias circuit 82 most preferably generate stable voltage reference and bias currents for analog circuits included in output circuit 54. Operating commands for controlling the timing of INS 10 are coupled by data bus 72 to digital controller/timer circuit 74, where digital timers and counters establish the specific stimulation parameters of INS 10 as well as various timing windows for controlling the operation of peripheral components disposed within input/output circuit 54.

Output pulse generator 96 provides electrical stimuli to desired nerve or nerve portion 8 through coupling capacitor 98 in response to a trigger signal provided by digital controller/timer circuit 74, when an externally transmitted stimulation command is received, or when a response to other stored commands is received.

By way of example, output amplifier 96 may correspond generally to an output amplifier disclosed in U.S. Pat. No. 4,476,868 to Thompson, hereby incorporated by reference herein in its entirety. The specific embodiments of output amplifier 96 identified herein are presented for illustrative purposes only, and are not intended to be limiting in respect of the scope of the present invention. The specific embodiments of such circuits may not be critical to practicing some embodiments of the present invention so long as they provide means for generating an appropriate train of stimulating pulses to desired nerve or nerve portion 8.

In various embodiments of the present invention, INS 10 may be programmably configured to operate so that it varies the rate at which it delivers stimulating pulses to desired nerve or nerve portion 8 in response to one or more selected outputs being generated. INS 10 may further be programmably configured to operate so that it may vary the morphology of the stimulating pulses it delivers. Numerous implantable electrical stimulator features and functions not explicitly mentioned herein may be incorporated into INS 10 while remaining within the scope of the present invention. Various embodiments of the present invention may be practiced in conjunction with one, two, three or more leads, or in conjunction with one, two, three, four or more electrodes disposed on each lead.

Leadless embodiments of the present invention are also contemplated, where one or more stimulation and/or sensing electrode capsules or modules are implanted at or near a desired nerve or nerve portion 8, and the capsules or modules deliver electrical stimuli directly to the selected site using a preprogrammed stimulation regime, and/or the capsules or modules sense electrical or other pertinent signals. Such capsules or modules are preferably powered by rechargeable batteries that may be recharged by an external battery charger using well-known inductive coil or antenna recharging means, and preferably contain electronic circuitry sufficient to permit telemetric communication with a programmer, to deliver electrical stimuli and/or sense electrical or other signals, and to store and execute instructions or data received from the programmer. Alternatively, in one embodiment of the present invention INS 10 is configured to recharge such a remotely positioned capsule or module by RF means on a periodic basis according to battery state of charge requirements measured or exhibited by such remote capsule or module.

Examples of methods and devices that may be adapted for use in the wireless devices and methods of the present invention include those described in U.S. Pat. No. 6,208,894 to Schulman et al. entitled "System of implantable devices for monitoring and/or affecting body parameters;" U.S. Pat. No. 5,876,425 to Schulman et al. entitled "Power control loop for implantable tissue stimulator;" U.S. Pat. No. 5,957,958 to Schulman et al. entitled "Implantable electrode arrays;" and U.S. patent application Ser. No. 09/030,106 filed Feb. 25, 1998 to Schulman et al. entitled "Battery-Powered Patient Implantable Device."

FIG. 3 shows a simplified anatomical view of the pelvic floor of a human patient, the locations of the pudendal and associated nerves therein, and an illustrative positioning of IMD 10 and electrical stimulation lead 16 and corresponding electrodes 20-23 and/or 40-43. FIG. 3 shows INS 10 implanted in an appropriate location within the patient, with lead 16 being implanted near or adjacent to one or more of prostatic plexus 32, hypogastric nerve 33, sacral nerves S1, S2, S3 and S4, nerves adjacent to prostate 34, pelvic splanchnic nerve 36 and/or pudendal nerve 26 to thereby effect therapeutic relief. Such relief is effected as a result of electrical stimulation signals being delivered to or near to or near one or more of such nerves 32, 33, S1, S2, S3, S4, 36, 26 and/or nerves adjacent to prostate gland 34 by electrodes 20, 21, 22, 23, 40, 41, 42 and 43. One, two, three, four or more electrodes 20, 21, 22 and 23 may be disposed at the distal end of lead 16. FIG. 3 shows eight electrodes located at the distal end of lead 16 near prostatic plexus 32. Consistent with the foregoing description, other lead locations and electrode configurations are of course possible and contemplated in the present invention.

Figure 4A:
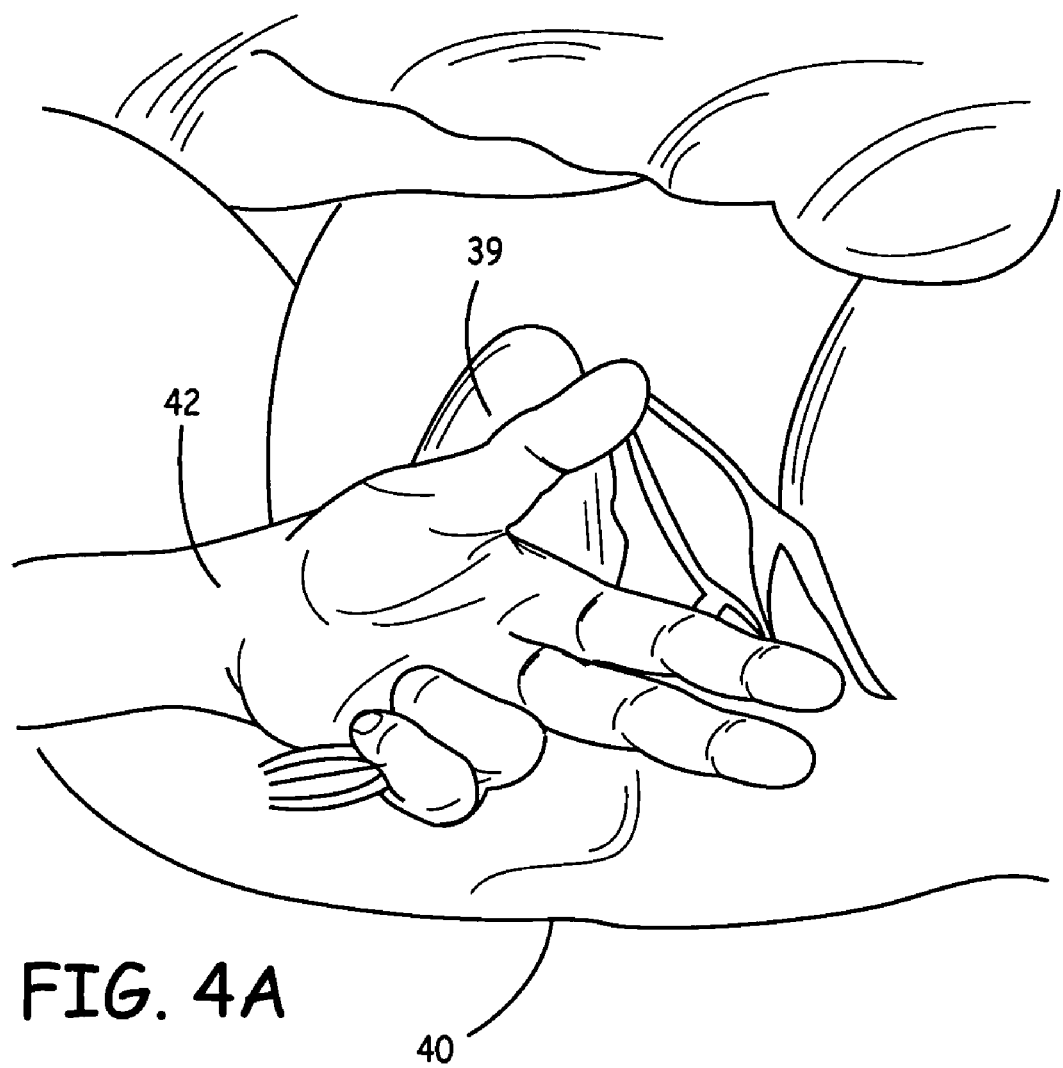
FIG. 4a shows one embodiment of a method of the present invention for determining an optimal electrical stimulation lead placement location in a female patient.
Figure 4B:
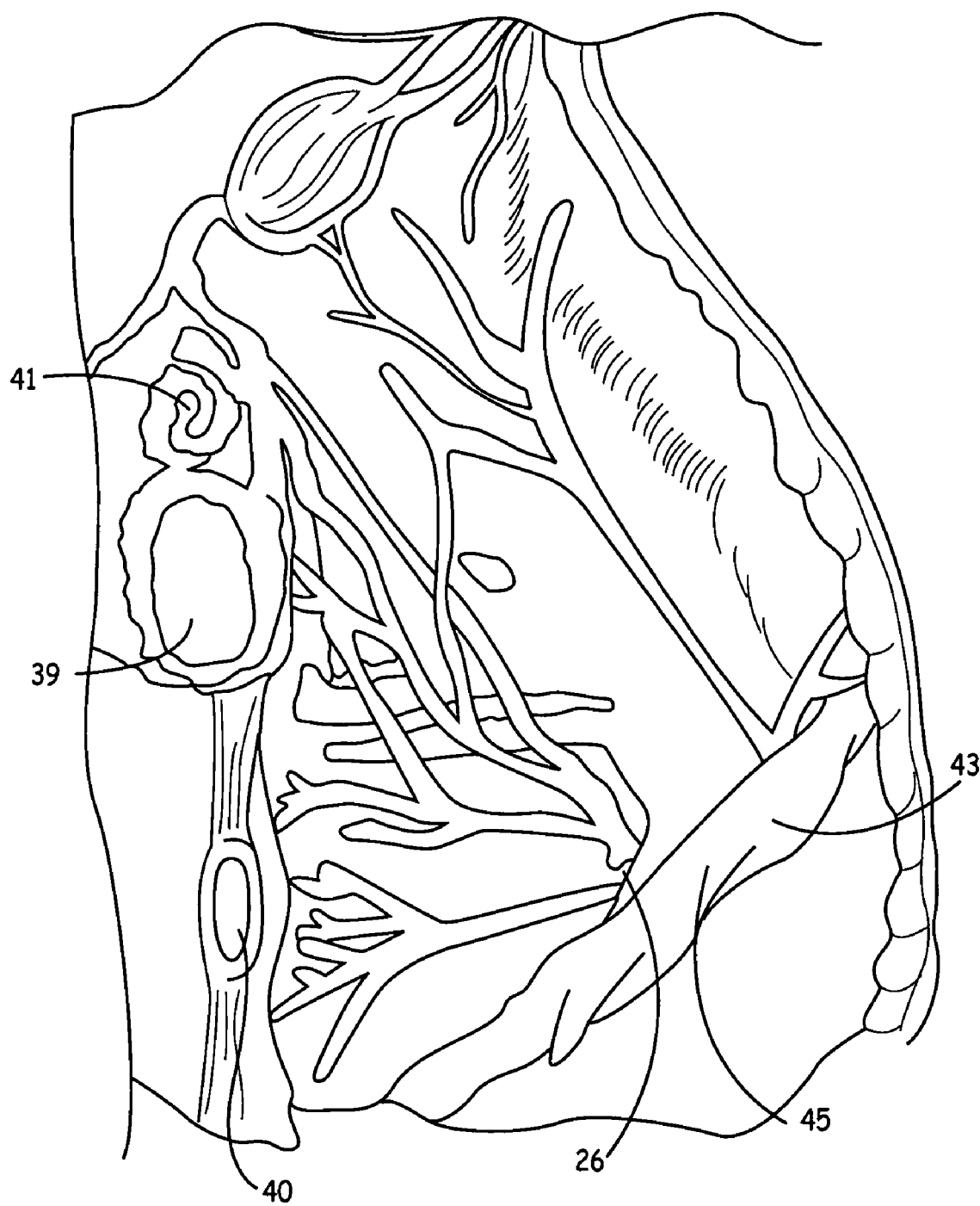
FIG. 4b shows a representative placement of a St. Mark's stimulation electrode on a hand of a physician.

FIG. 4a shows one embodiment of a method of the present invention for determining an optimal electrical stimulation lead placement location in a female patient. A physician employs gloved finger 42 to insert St. Mark's electrode 59 in female patient's vagina 39. Test stimulation pulses are provided to stimulation electrode(s) disposed at the distal end of St. Mark's electrode 59 to establish an optimal electrical stimulation location near or adjacent to desired nerve or nerve portion 8 within the patient, as well as to establish optimal stimulation pulse parameters, more about which we say below. When mounted on a physician's gloved hand 42, St. Mark's electrode 59 is preferably configured such that the one or more stimulation electrodes disposed thereon are located near the distal end of the physician's index finger. FIG. 4b shows a representative placement of St. Mark's stimulation electrode 59 on gloved hand 42 of a physician.

Figure 4C:
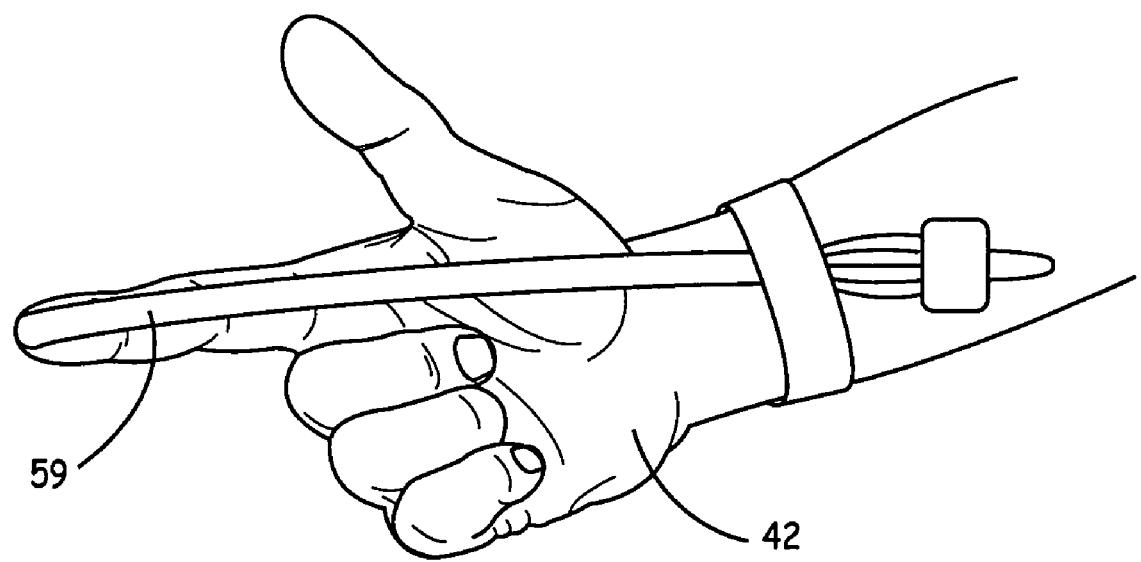

FIG. 4c shows a simplified anatomical view of the locations of pudendal nerve 26 and associated nerves and nerve portions 8 in the patient of FIG. 4a. As shown in FIG. 4b, pudendal nerve 26 and associated nerves and nerve portions 8 are or may be located, depending on individual patient anatomical details, in relatively close proximity to one or more of urethra 41, sacrospinal ligament 43, vagina 39, anus 40 and pudendal canal/Alcock's canal 45. Note that in female patients anus 40 provides an alternative to vagina 39 as a means of accessing optimal electrical stimulation sites near or adjacent to pudendal nerve 26 and associated nerves and nerve portions 8. In male patients, anus 40 provides the preferred means of accessing such sites.

FIG. 5 shows further simplified anatomical views of the pelvic floor and the locations of pudendal nerve 26 and associated nerves and nerve portions 8 therein. As shown in FIG. 5, pudendal nerve 26 innervates the pelvic floor muscle and sphincters, enters the ischiorectal fossa after passing behind sacrospinal ligament 43, and then travels through Alcock's canal 45 to give rise to three different nerve branches: the inferior rectal nerve, the inferior perineal nerve and the inferior dorsal nerve. The inferior rectal nerve innervates the external anal sphincter (EAS). The conduction of motor fibers is preferably tested by electrically stimulating a motor nerve along its peripheral course and recording the electrical response from a muscle innervated by that nerve. In such fashion, conduction in the motor fibers of pudendal nerve 26 is assessed by stimulating pudendal nerve 26 or portions or branches associated therewith. In one embodiment of the present invention, the latency or delay from the onset of stimulation to the onset of corresponding muscle response in the EAS is measured and quantified.

Figure 6:
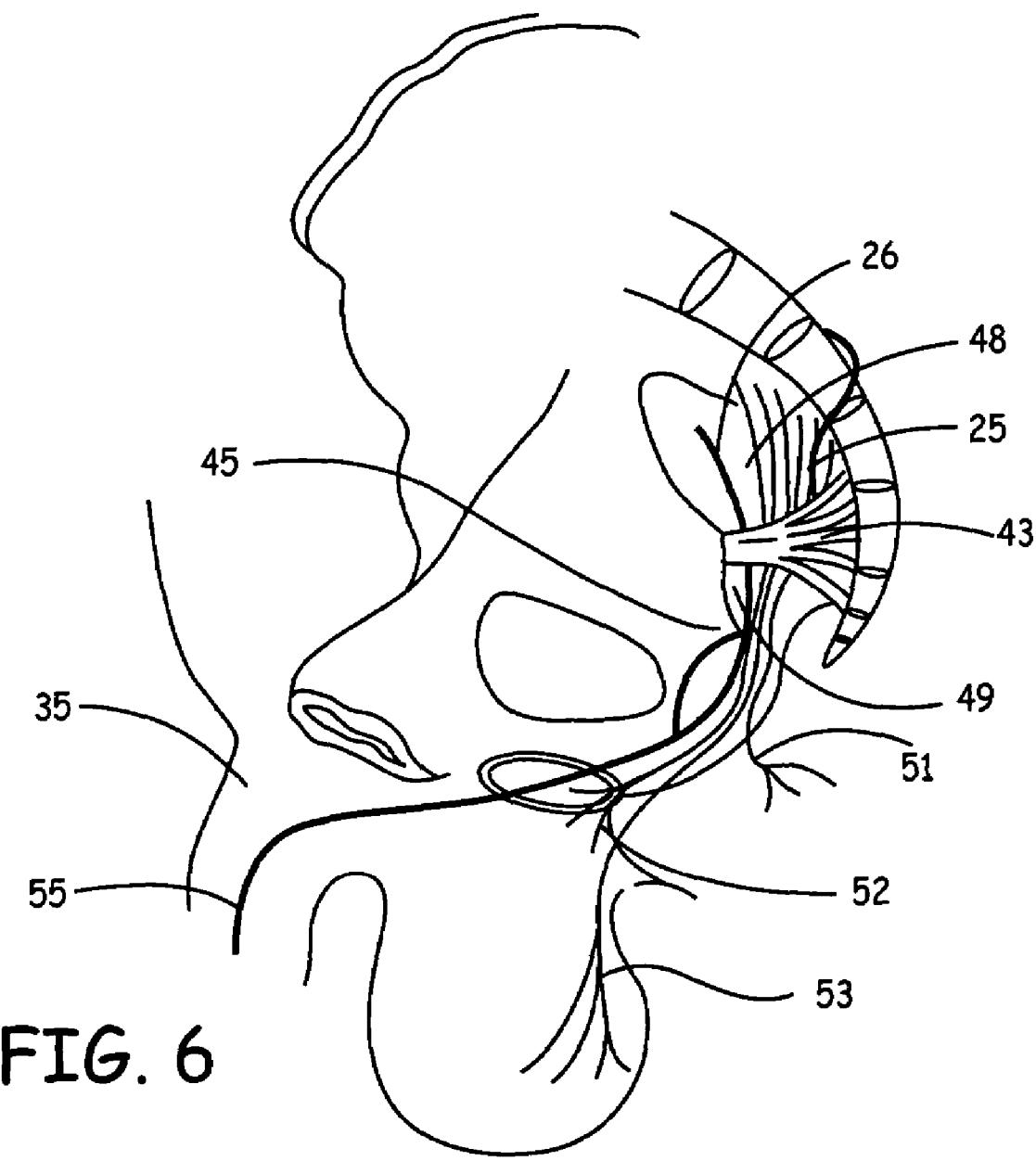
FIG. 6 shows a simplified male anatomical view of the pelvic floor and the locations of the pudendal and associated nerves therein.

FIG. 6 shows a simplified male anatomical view of the pelvic floor and the locations of the pudendal nerve 26 and nerves associated therewith, where in accordance with some embodiments of the present invention leads 16 and/or 18 and electrodes 20-23 and/or 40-43 may be attached, connected or implanted in proximity thereto. Pudendal nerve 26 may be seen to extend downwardly past sacrospinal ligament 43, greater sciatic foramen 48, and lesser sciatic foramen 49, and thereafter to branch into inferior rectal nerves 51, perineal nerves 52, scrotal nerves 53 and dorsal nerve 55 of penis 35.

Figure 7:
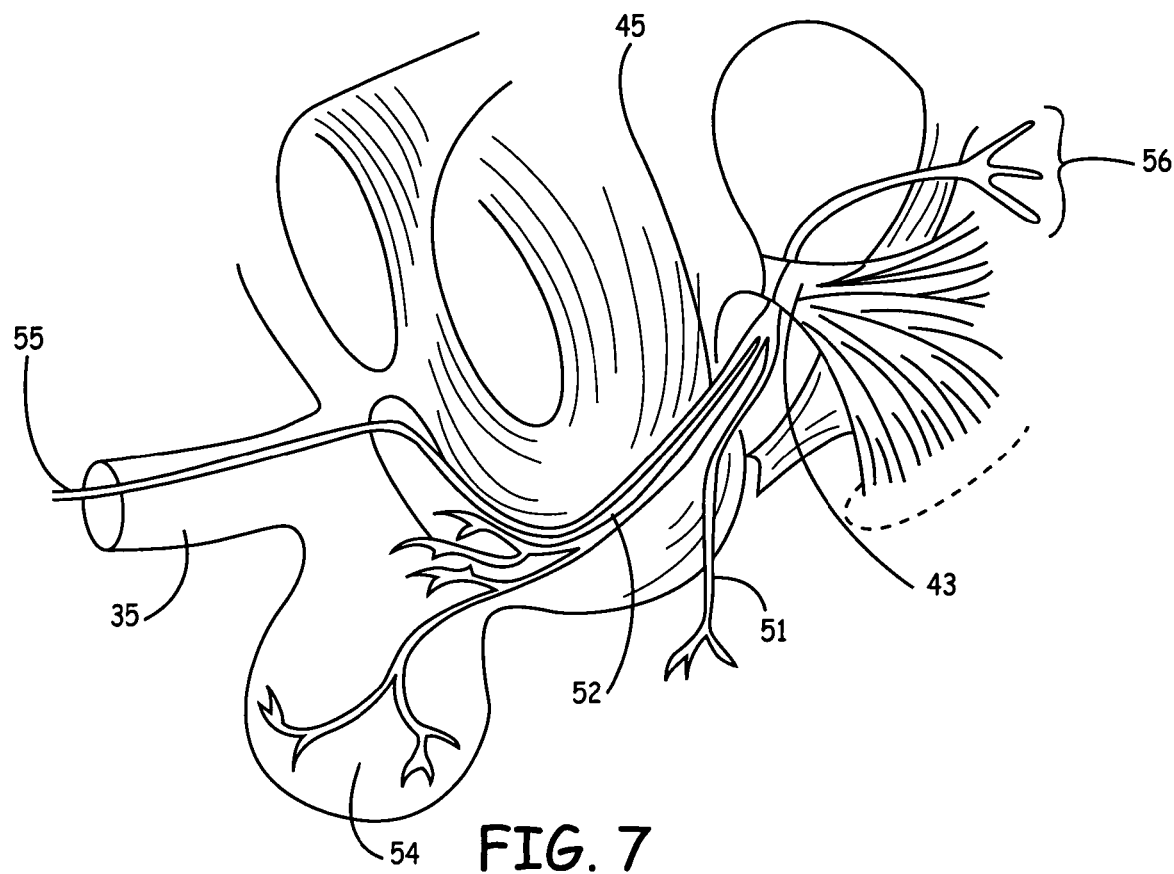
FIG. 7 shows another simplified male anatomical view of the pelvic floor and the locations of the pudendal and associated nerves therein.

FIG. 7 shows another simplified male anatomical view of the pelvic floor and the locations of the pudendal nerve 26 and some branches associated therewith, where leads 16 and/or 18 and electrodes 20-23 and/or 40-43 of the present invention may be attached, connected or implanted in proximity thereto. Nerves 56 may be seen to extend upwardly from proximity to sacrospinal ligament 43. Nerves 51 and 52 pass through Alcock's Canal 45 and thereafter branch into perineal nerves 52, scrotal nerves 53 and dorsal nerve 55 of penis 35.

Figure 8:
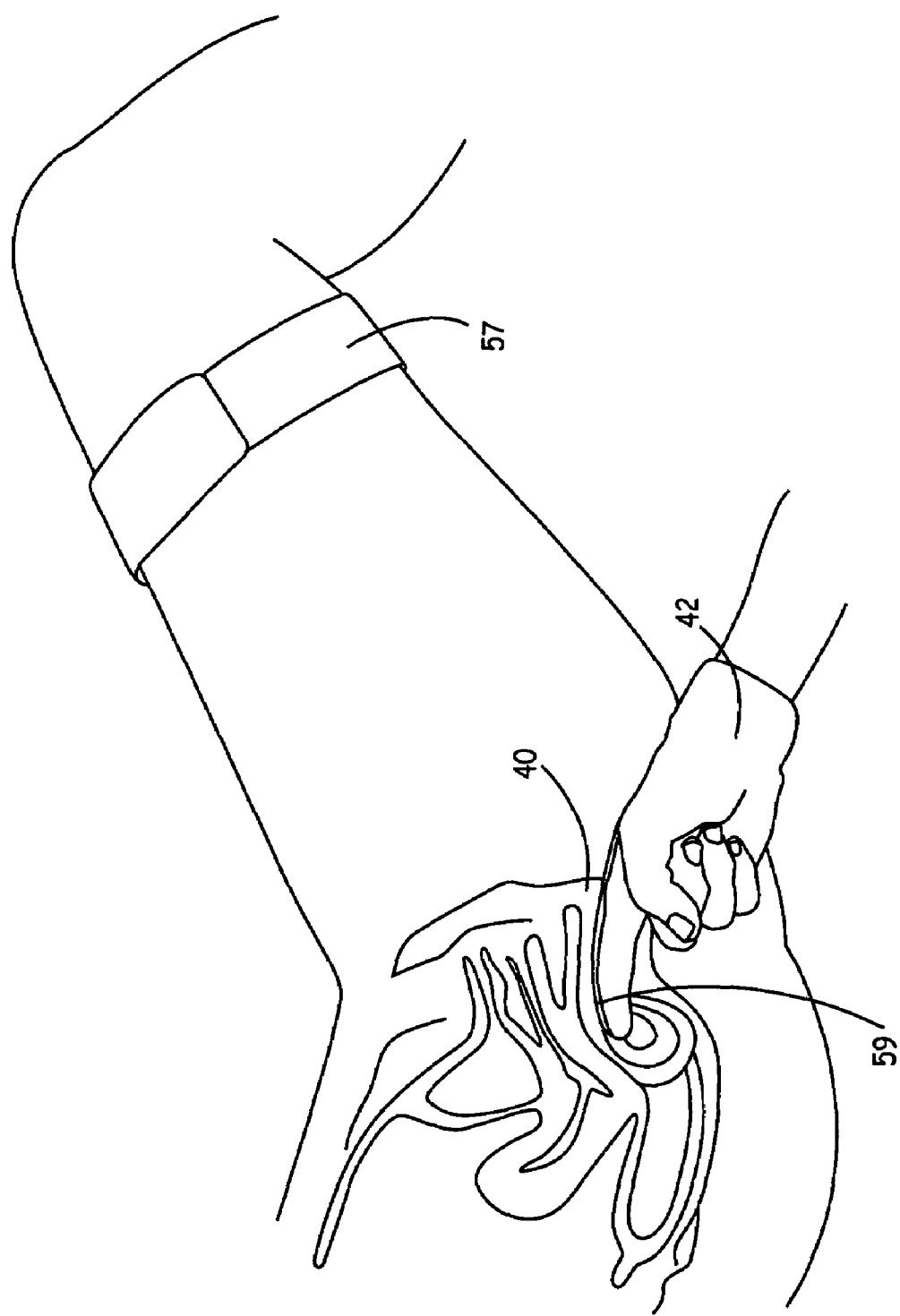
FIG. 8 shows one embodiment of a method of the present invention for locating the pudendal nerve or its branches in a female patient.

FIG. 8 shows one aspect of a method of the present invention for locating pudendal nerve 26 and/or portions or branches associated therewith in a female patient. Gloved fingers 42 and St. Mark's electrode 59 are inserted in anus/rectum 40 to effect transrectal stimulation of pudendal nerve 26 and/or portions or branches associated therewith. St. Mark's electrode 59 is employed, in conjunction with ground electrode 57, to electrically stimulate a distal portion of pudendal nerve 26 and/or portions or branches associated therewith. The method illustrated in FIG. 8 has been discovered to be particularly efficacious in respect of permitting that portion of pudendal nerve 26 disposed within or near Alcock's Canal 45, as well as the three branches thereof which project upwardly, to be electrically stimulated effectively and precisely. The patient is preferably positioned in a lithotomy position, and his or her thigh is grounded electrically by means of ground electrode 57.

In a preferred mode of the present invention, the electrophysiologic test corresponding to the method of FIG. 8 begins by inserting a concentric electromyographic (EMG) recording needle or electrode into the intermediate portion of the left or right subcutaneous portion of the patient's External Anal Sphincter) muscle (or "EAS"), and recording data representative of EMG activity of corresponding to the EAS at rest, during voluntary contraction, and during reflex contraction. The index finger of gloved hand 42 having St. Mark's electrode 59 disposed thereon is then inserted into anus/rectum 40 and ischial spine 44 is palpitated.

Most preferably, such recording is accomplished using a 500 msec. time window, a sensitivity of 100 μV, a lower frequency of 20 Hz and an upper frequency of 10 KHz, and employs a KEYPOINT PORTABLE neurodiagnostic 2-channel EMG, NCS and EP recording and analysis system manufactured by MEDTRONIC. The Instructions for Use Manual of such system is hereby incorporated by reference herein, in its entirety. Myriad other recording and stimulation parameters and methods may be employed in accordance with the present invention.

In a preferred embodiment of the present invention, typical stimulation parameters include applying square-wave stimulation signals across electrodes 59 and 57, such stimulation signals having a 0.10 msec. duration and a current amplitude which gradually increases from 0 mA to 100 mA. Electrical response of the EAS to the thus applied electrical stimulation is sensed by the concentric EMG needle, and recorded by an appropriate recording apparatus connected thereto. Preferably, the sensed signals are stored for subsequent detailed analysis. Typical sensing parameters for the recording apparatus and concentric needle are 5 μV sensitivity, a time window of 100 ms, a lower frequency of 100 Hz and an upper frequency of 2 KHz.

Figure 9:
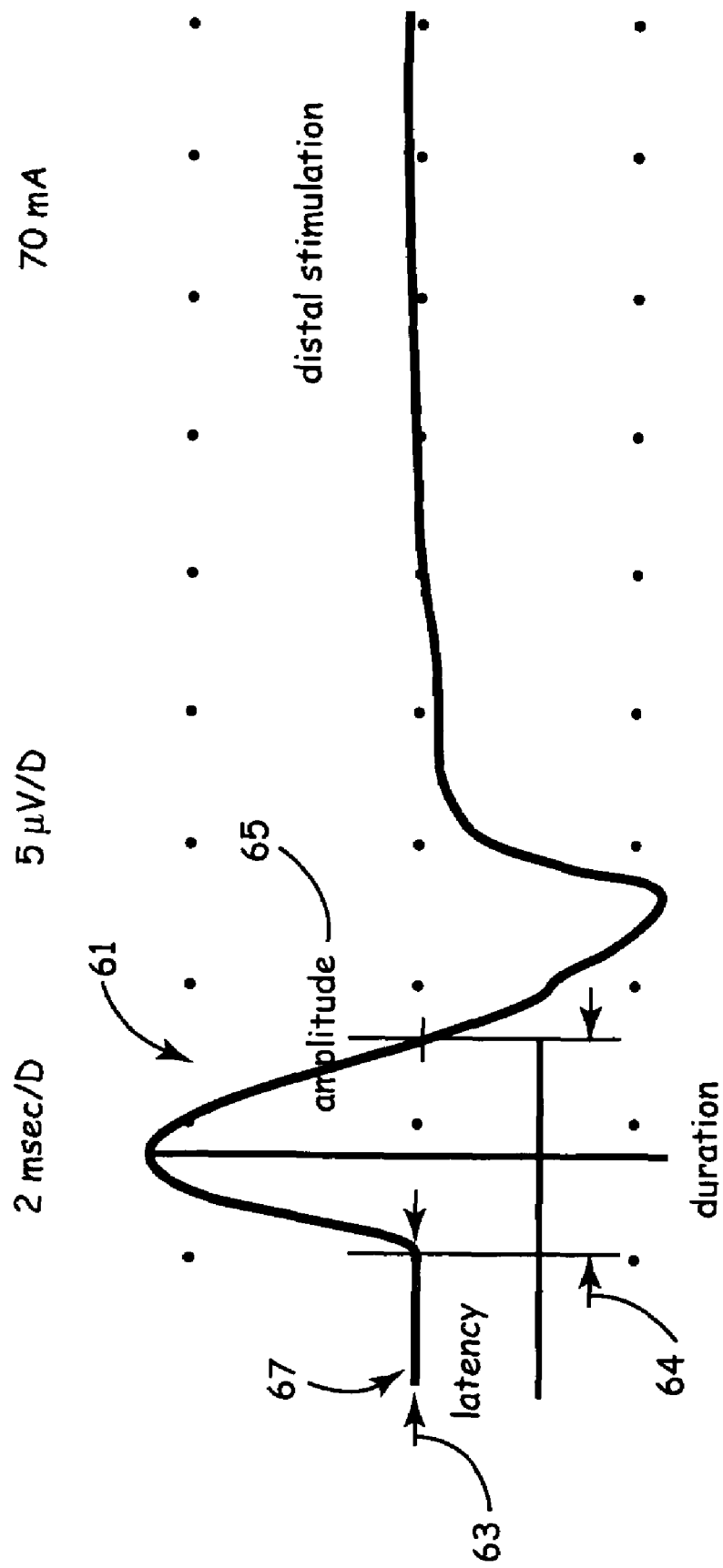
FIG. 9 shows a representative Compound Muscle Action Potential (CMAP) signal resulting from stimulating the pudendal nerve.

FIG. 9 shows a representative Compound Muscle Action Potential (CMAP) signal resulting from successfully stimulating pudendal nerve 26 in accordance with one method of the present invention. It has been determined that the EAS provides a nearly optimal site for sensing CMAP signals. Note, however, that other stimulation and/or sensing sites, such as pudendal nerve 26, prostate 34, pelvic floor 31, colon 37, superior hypogastric nerve 33, pelvic splanchnic nerve 36, bladder 38, prostatic plexus 32, vagina 39, anus/rectum 40, urethra 41, penis dorsal nerve 55, inferior rectal nerves 51, perineal nerves 52, scrotal nerves 53, scrotum 54, sacral nerves 56, Alcock's Canal 45, sacro-tuberous ligament 46, ischial tuberosity 47, greater sciatic foramen 48 and lesser sciatic foramen 49 may also be employed in the present invention.

As illustrated in FIG. 9, some parameters that may be measured in sensed CMAP signals originating from the EAS in response to appropriately applied stimulation signals include: (a) CMAP signal amplitude (e.g., peak-to-peak, RMS, etc.); (b) CMAP signal latency (or the difference in time between the moment the stimulation signal is applied to the stimulation site and the beginning of the corresponding response or sensed CMAP signal); (c) CMAP signal duration; (d) area beneath the CMAP signal curve; (e) CMAP signal spectral characteristics (e.g., spectral power derived from autocorrelation computations, bandwidth, upper and lower cut-off frequencies, filtering, etc.), and the phase or phases of a CMAP signal or signals.

As employed herein, the term "signal latency" means the period of time between the time distal stimulation is initiated and the time that the onset of the corresponding response occurs. Signal latency is related to a number of factors, including, but not limited to: (a) conduction velocity of the distal nerve segment; (b) conduction velocity of neuromuscular transmission; and (c) time required for muscle depolarization. As shown in FIG. 9, signal latency 63 of the EAS response is most preferably measured between the time of the onset of the distal stimulation and the time of the onset of the corresponding response. Signal latency 63 represents the terminal motor latency of pudendal nerve 26 to the EAS. By slowing movement of electrode 59, the optimum position for stimulation of pudendal nerve 26 is found as recognized when a maximum signal amplitude 65 and shortest signal latency 63 of the evoked EAS response appear on the oscilloscope of the EMG measurement apparatus. Signal amplitude 65 of the motor response depends on several factors, including, but not limited to, the number of functioning nerve fibers, the integrity of NMJ, the number of functioning muscle fibers in the muscle and the synchrony of firing.

Figure 10A:
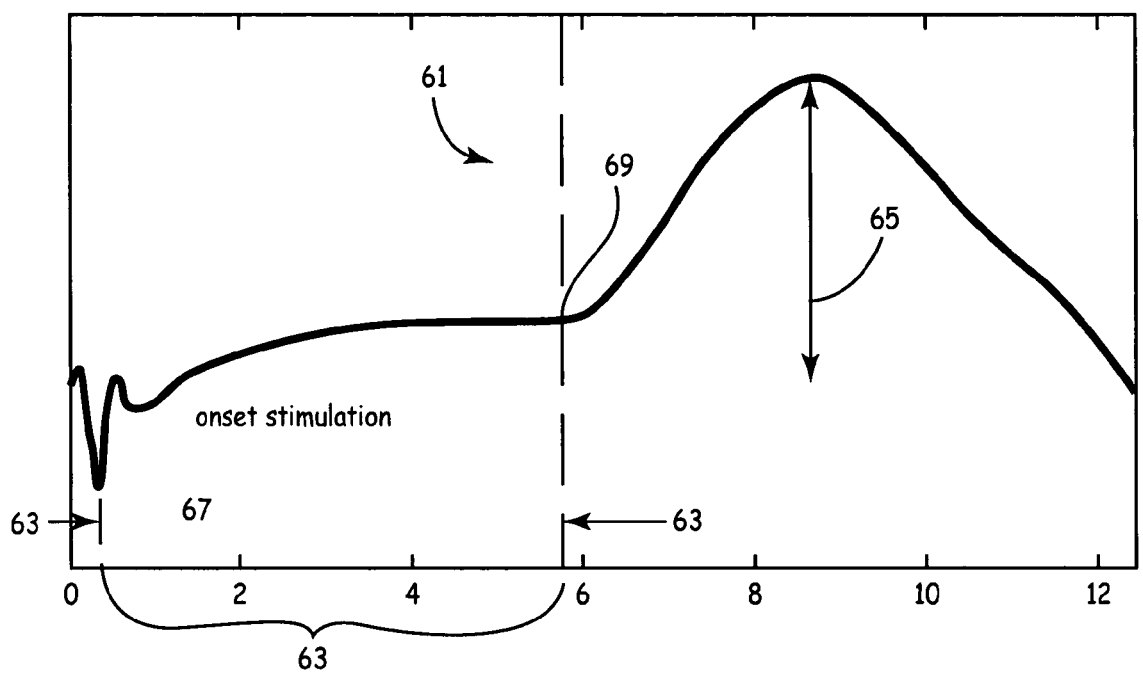
FIGS. 10a and 10b illustrate representative latency characteristics of CMAP signals resulting from stimulating the pudendal nerve.
Figure 10B:
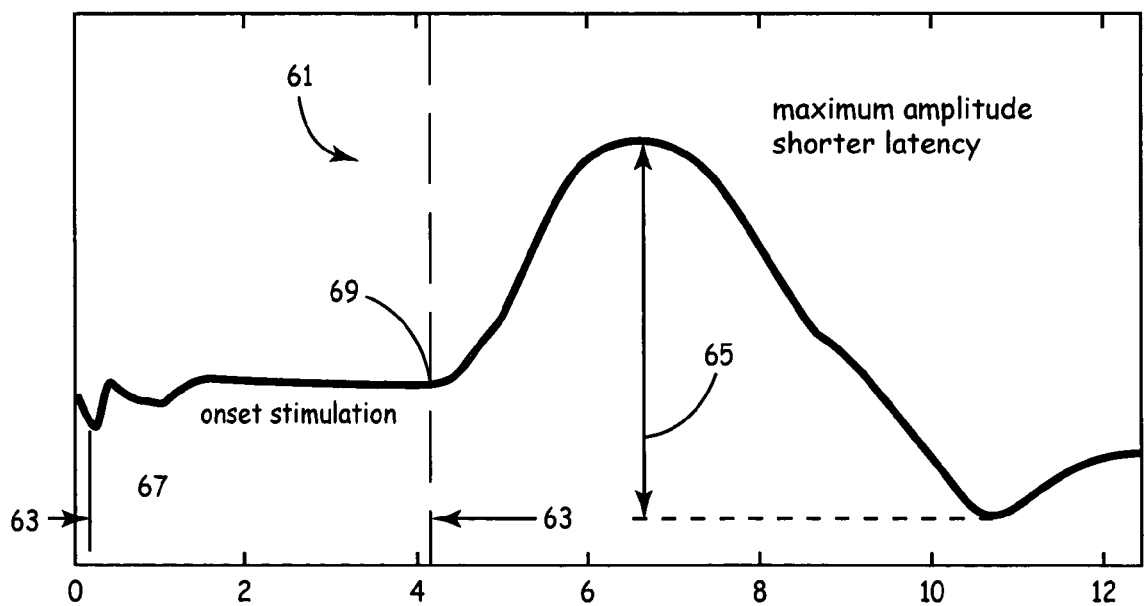

FIGS. 10a and 10b illustrate typical latency characteristics of CMAP signals resulting from stimulating pudendal nerve 26 in accordance with one embodiment of the present invention. In FIG. 10a, a relatively poor distal stimulation site results in a broad, low-frequency CMAP signal having indistinct CMAP onset 69 and relatively low amplitude 65. In FIG. 10b, a better distal stimulation site results in a CMAP signal having a more narrow peak, higher amplitude 65, and more distinct CMAP onset 69.

Figure 11:
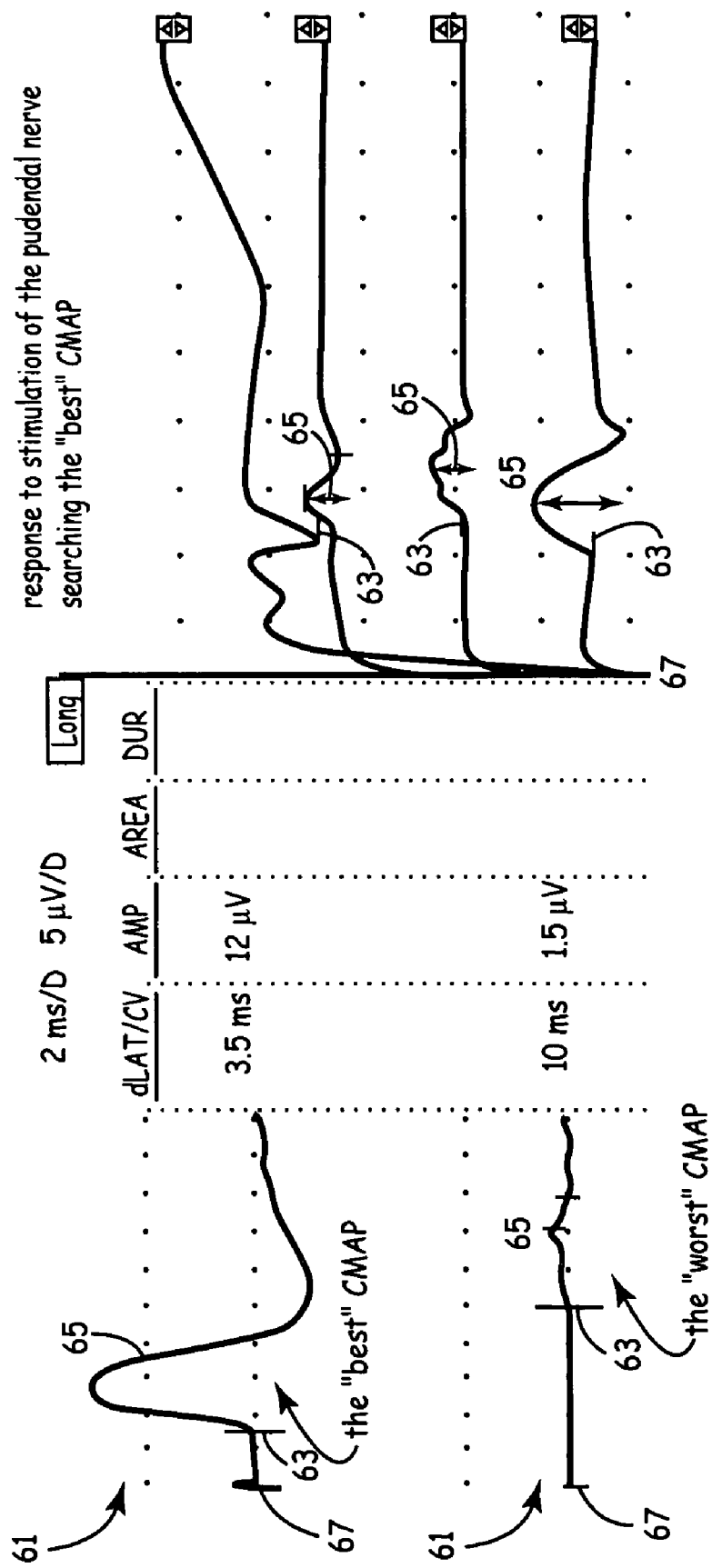
FIG. 11 illustrates representative CMAP signals resulting from stimulating the pudendal nerve in different locations.

FIG. 11 illustrates further representative CMAP signals resulting from stimulating the pudendal nerve in different locations. On the left-hand side of FIG. 11 are shown "best" (top) and "worst" (bottom) CMAP signals obtained with different distal stimulation sites. On the right-hand side is shown a series of CMAP signals, each such signal obtained using a different distal stimulation site. The bottom-most of the right-hand CMAP signals is seen to provide the best response with highest CMAP signal amplitude 65 and most distinct onset 63. In accordance with such a method of the present invention, the best or optimum CMAP signal so obtained provides a physician with the information required to determine an optimum distal stimulation site for delivering the desired therapy.

It is important to note that the present invention may be practiced using stimulation electrodes other than concentric needles. For example, urethral ring electrodes, anal plug electrodes, surface electrodes, anal sphincter surface electrode, vaginal surface electrode, or any other type of electrode suitable for measuring EMG signals may be employed. The URO PRIMER: A PRACTICAL REFERENCE FOR URODYNAMIC EXAMINATIONS published by MEDTRONIC DANTEC is hereby incorporated by reference herein in its entirety, and provides examples of the use of the foregoing electrode types.

Figure 12A:
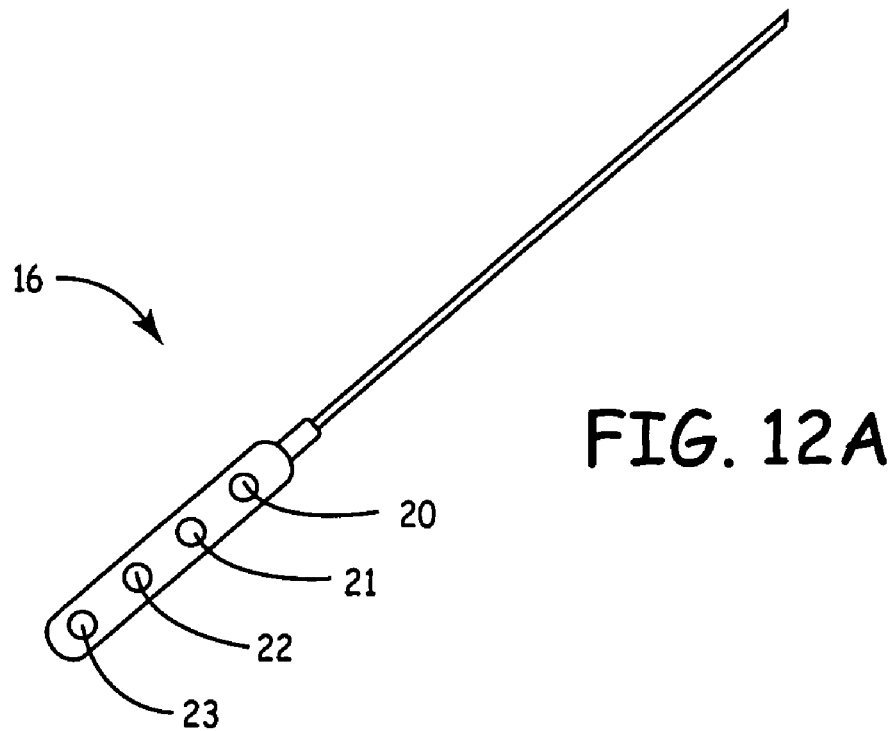
FIGS. 12A through 12E show various embodiments of the distal end of lead 16 of the present invention.

FIGS. 12A through 12E show various embodiments of a distal end of medical electrical lead 16 of the present invention. In FIG. 12A, lead 16 is a paddle lead having electrodes 20-23 arranged along an outwardly facing planar surface. Such a paddle lead 16 is preferably employed to stimulate peripheral nerves.

Figure 12B:
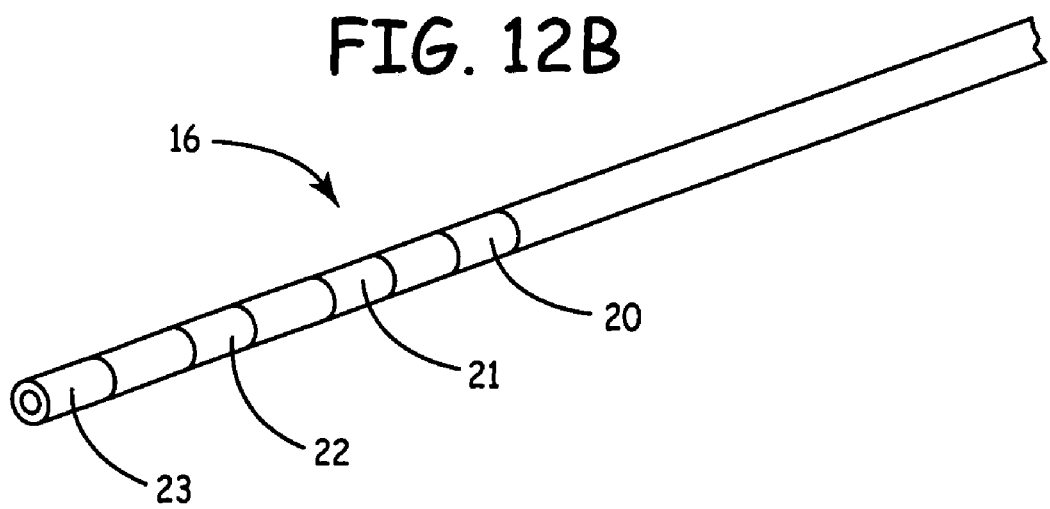

In FIG. 12B, lead 16 is a conventional quadrapolar lead having no pre-attached anchoring mechanism 19. Electrodes 20-23 are cylindrical in shape and extend around the circumference of the lead body.

Figure 12C:
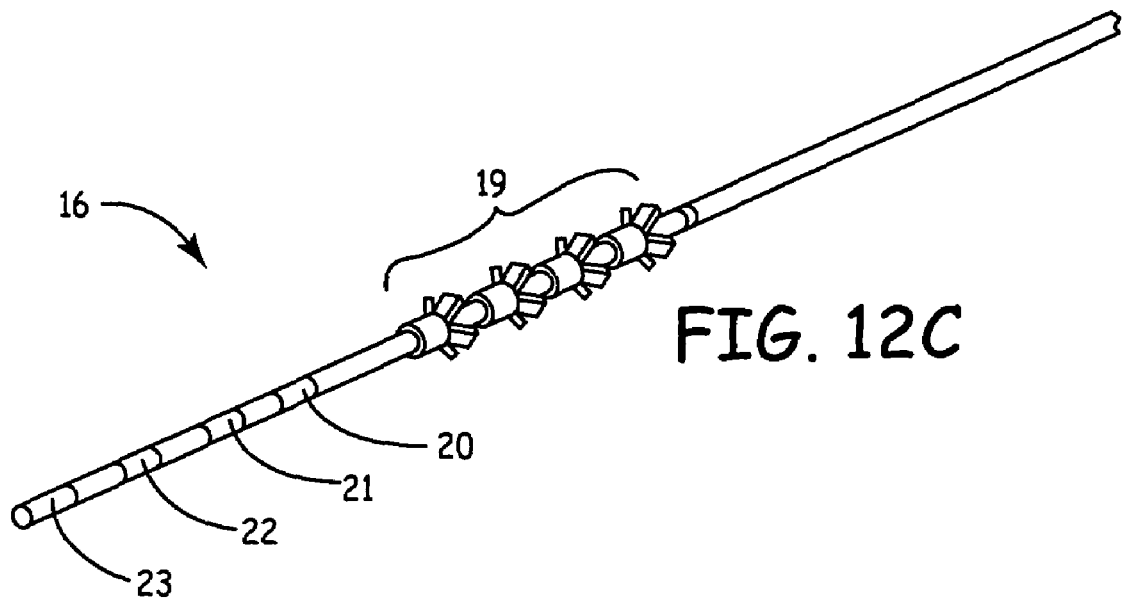

In FIG. 12C, lead 16 is a quadrapolar lead having tined lead anchors 19. Tines 19 may be formed from flexible or rigid biocompatible materials in accordance with the desired application. Representative examples of some tined and other types of leads suitable, adaptable or modifiable for use in conjunction with the systems, methods and devices of the present invention include those disclosed in U.S. patent application Ser. Nos. 10/004,732 entitled "Implantable Medical Electrical Stimulation Lead Fixation Method and Apparatus" and Ser. No. 09/713,598 entitled "Minimally Invasive Apparatus for Implanting a Sacral Stimulation Lead" to Mamo et al., as well as those disclosed in U.S. Pat. No. 3,902,501 to Citron entitled "Endocardial Lead," U.S. Pat. No. 4,106,512 to Bisping entitled "Transvenously Implantable Lead," U.S. Pat. No. 5,300,107 to Stokes entitled "Universal Tined Myocardial Pacing Lead."

Figure 12D:
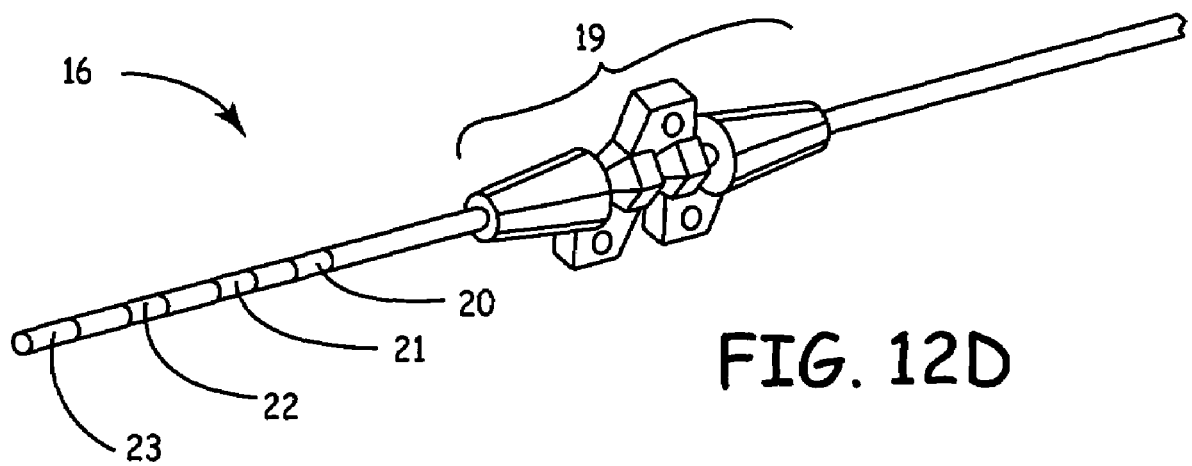

In FIG. 12D, lead 16 is a quadrapolar lead having pre-attached suture anchor 19.

Figure 12E:
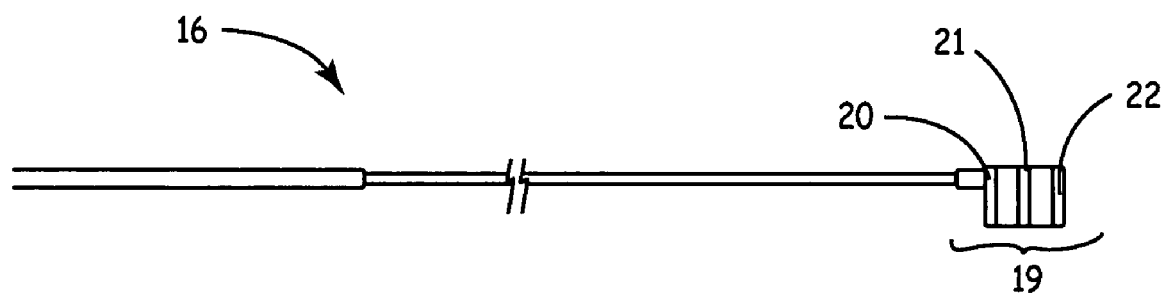

In FIG. 12E, lead 16 is a tri-polar cuff electrode, where cuff/anchor 19 is wrapped around desired nerve or nerve portion 8 to thereby secure the distal end of lead 16 to the nerve and position electrodes 20-22 against or near nerve or nerve portion 8. The Medtronic Model No. 3995 cuff electrode lead is one example of a lead that may be adapted for use in the present invention, the Instructions for Use manual of which is hereby incorporated by reference herein in its entirety.

Leads 16 and 18 are preferably less than about 5 mm in diameter, and most preferably less than about 1.5 mm in diameter. Polyurethane is a preferred material for forming the lead body of leads 16 and 18, although other materials such as silicone may be employed. Electrical conductors extending between the proximal and distal ends of leads 16 and 18 for supplying electrical current to the electrodes are preferably formed of coiled, braided or stranded wires comprising an MP35N platinum-iridium alloy. Electrodes 20, 21, 22 and 23 may be ring electrodes, coiled electrodes, electrodes formed from portions of wire, barbs, hooks, spherically-shaped members, helically-shaped members, or may assume any of a number of different structural configurations well known in the art.

Inter-electrode distances on leads 16 and 18 are preferably about 3 mm, but other inter-electrode distances may be employed such as about 1 mm, about 2 mm, about 4 mm, about 5 mm, about 6 mm, about 7 mm, about 8 mm, about 9 mm, about 10 mm, about 12 mm, about 14 mm, about 16 mm, about 18 mm, about 20 mm, about 25 mm, about 30 mm.

Preferred surface areas of electrodes 20, 21, 22 and 23 range between about 1.0 sq. mm and about 100 sq. mm, between about 2.0 sq. mm and about 50 sq. mm, and about 4.0 sq. mm and about 25 sq. mm.

Preferred lengths of electrodes 20, 21, 22 and 23 range between about 0.25 mm and about 10 mm, between about 0.50 mm and about 8 mm, and about 1.0 mm and about 6 mm.

Table 2 below shows representative values of the electrode surface areas and lengths for the Medtronic Model No. 3080 lead that may be adapted for use in various embodiments of the present invention. Electrodes 20, 21, 22 and 23 are preferably formed of platinum, although other metals and metal alloys may be employed such as stainless steel or gold.

TABLE 2

Medtronic Model No. 3080 Lead Electrode Surface Areas and Lengths

| Electrode length (mm) | Electrode Surface Area ($mm^2$) | Electrode Surface Area per Lead (4 electrodes) |
|---|---|---|
| 0.5 | 2.0 | 8.0 |
| 1 | 4.0 | 16.0 |
| 2 | 8.0 | 31.9 |
| 3 | 12.0 | 47.9 |
| 4 | 16.0 | 63.8 |
| 5 | 19.9 | 79.8 |
| 6 | 23.9 | 95.8 |
| 7 | 27.9 | 111.7 |
| 8 | 31.9 | 127.7 |
| 9 | 35.9 | 143.6 |
| 10 | 39.9 | 159.6 |

The distal portion of lead 16 extends to a target site or position near a desired nerve or nerve portion 8, and is preferably held in such position by lead anchor 19. Note that lead anchor 19 may assume any of a number of different structural configurations such one or more suture sleeves, tines, barbs, hooks, a helical screw, tissue in-growth mechanisms, adhesive or glue.

One, two, three, four or more electrodes 20, 21, 22 and 23 may be disposed at the distal end of lead 16 and/or lead 18. Electrodes 20, 21, 22 and 23 are preferably arranged in an axial array, although other types of arrays may be employed such as inter-lead arrays of electrodes between the distal ends of leads 16 and 18 such that nerves or nerve portions 8 disposed between leads 16 and 18 may be stimulated.

Leads 16 and 18 preferably range between about 4 inches and about 20 inches in length, and more particularly may be about 6 inches, about 8 inches, about 10 inches, about 12 inches, about 14 inches, about 16 inches or about 18 inches in length, depending on the location of the site to be stimulated and the distance of INS 10 from such site. Other lead lengths such as less than about 4 inches and more than about 20 inches are also contemplated in the present invention.

Figure 13A:
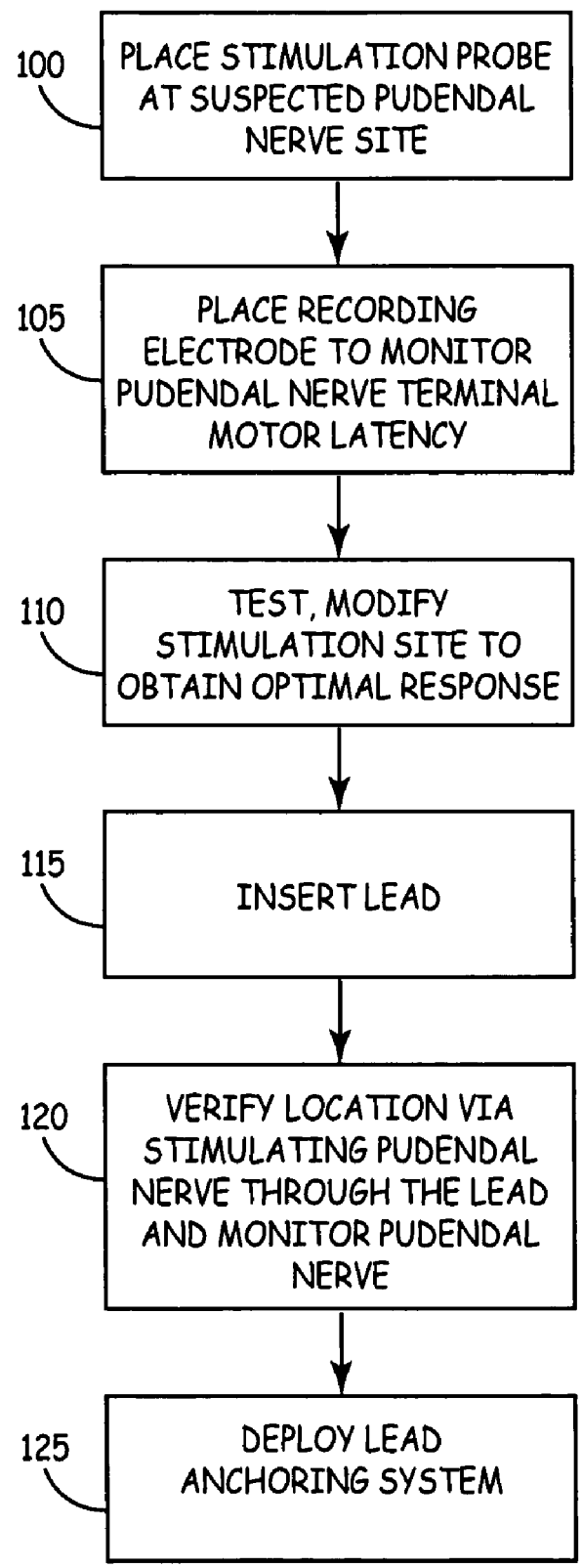
FIGS. 13a and 13b show flow diagrams according to several embodiments of methods of the present invention for stimulating the pudendal nerve.
Figure 13B:
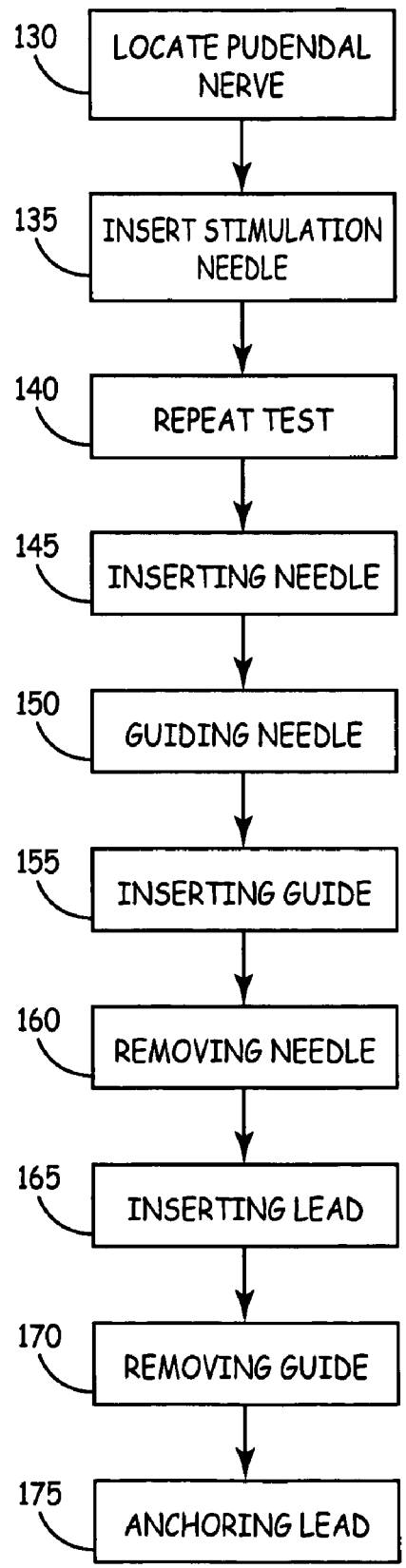

FIGS. 13a and 13b show flow diagrams according to several embodiments of methods of the present invention for stimulating the pudendal nerve. In FIG. 13a, step 110 is employed to determine one or more desired nerve stimulation locations near or at one or more of prostatic nerve plexus 32, hypogastric nerve 33, pelvic splanchnic nerve 36, pudendal nerve 26, prostate gland 34, vesicle nerve plexus 30, pelvic nerve plexus 28, sacral nerve S1, sacral nerve S2, sacral nerve S3, sacral nerve S4, and/or sacral nerve S5. Step 120 is employed to implant lead 16 and electrodes 20, 21, . . . n near or at the desired nerve stimulation site(s). Note that that methods of the present invention further contemplate the placement and implantation of multiple leads. Step 130 is employed to implant INS 10 in an appropriate location within the patient such that the proximal end of lead 16 may be operably connected thereto and such that INS 10 is placed in such a location that discomfort and the risk of infection to the patient are minimized. Step 140 is employed to operably connect INS 10 to lead 16, which may or may not require the use of optional lead extension 15 and lead connector 13. In Step 150, INS 10 is activated and stimulation pulses are delivered to electrodes 20, 21, . . . n through lead 16 to the desired nerve stimulation location. In step 160, the electrical pulse stimulation parameters are adjusted to optimize the therapy delivered to the patient. Such adjustment may entail one or more of adjusting the number or configuration of electrodes or leads used to stimulate the selected location, pulse amplitude, pulse frequency, pulse width, pulse morphology (e.g., square wave, triangle wave, sinusoid, biphasic pulse, tri-phasic pulse, etc.), times of day or night when pulses are delivered, pulse cycling times, the positioning of the lead or leads, and/or the enablement or disablement of "soft start" or ramp functions respecting the stimulation regime to be provided.

Representative ranges of preferred electrical pulse stimulation parameters capable of being delivered by INS 10 through leads 16 and 18 include the following:

| | |
|---|---|
| Frequency: | Between about 50 Hz and about 100 Hz; Between about 10 Hz and about 250 Hz; and Between about 0.5 Hz and about 500 Hz. |
| Amplitude: | Between about 1 Volt and about 10 Volts; Between about 0.5 Volts and about 20 Volts; and Between about 0.1 Volts and about 50 Volts. |
| Pulse Width: | Between about 180 microseconds and about 450 microseconds; Between about 100 microseconds and about 1000 microseconds; and Between about 10 microseconds and about 5000 microseconds. |

In the event multiple signals are employed to stimulate a desired site, the spatial and temporal phase between the signals may be adjusted or varied to produce the desired stimulation pattern or sequence. That is, in the present invention beam forming and specific site targeting via electrode array adjustments are specifically contemplated. Electrode configurations, arrays and stimulation patterns and methods similar to those disclosed by Holsheimer in U.S. Pat. No. 6,421,566 entitled "Selective Dorsal Column Stimulation in SCS, Using Conditioning Pulses," U.S. Pat. No. 5,643,330 entitled "Multichannel Apparatus for Epidural Spinal Cord Stimulation" and U.S. Pat. No. 5,501,703 entitled "Multichannel Apparatus for Epidural Spinal Cord Stimulator," the respective entireties of which are hereby incorporated by reference herein, may also be adapted or modified for use in the present invention. Electrode configurations, arrays, leads, stimulation patterns and methods similar to those disclosed by Thompson in U.S. Pat. No. 5,800,465 entitled "System and Method for Multi-site Steering of Cardiac Stimuli," the entirety of which is hereby incorporated by reference herein, may also be adapted or modified for use in the present invention to permit the steering of electrical fields. Thus, although FIG. 1 shows four electrodes located at the distal end of lead 16 near sacral nerve S3, other lead locations and electrode configurations are possible and contemplated in the present invention.

In addition, in the present invention it is contemplated that drugs be delivered to specific sites within a patient using well known fully implantable drug pump devices in combination with providing electrical stimulation to the nerves or nerve portions described above. According to such a method, the drug pump may be incorporated into the same housing as INS 10, or be separate therefrom in its own hermetically sealed housing. The drug catheter attached to the implantable drug pump through which the drug is delivered to the specific site may also be incorporated into lead 16 or 18, or may be separate therefrom. Drugs or therapeutic agents delivered in accordance with this method include, but are not limited to, antibiotics, pain relief agents such as demerol and morphine, radioactive or radio-therapeutic substances or agents for killing or neutralizing cancer cells, genetic growth factors for encouraging the growth of healthy tissues, drugs for facilitating or encouraging penile or clitoral engorgement, and the like.

Also hereby incorporated by reference herein in its entirety is U.S. patent application No. 20020082665A1 to Haller et al. published Jun. 27, 2002 entitled "System and Method of Communicating between an Implantable Medical Device and a Remote Computer System or Health Care Provider." In the present invention it is further contemplated that the methods and devices described hereinabove be extended to include the various communication systems of Haller et al. for at least one of monitoring the performance of INS 10 and/or an implantable drug pump implanted within the body of a patient, monitoring the health of the patient and remotely delivering an electrical stimulation and/or drug therapy to the patient through INS 10 and/or the optional implantable drug pump, INS 10 or the implantable drug pump being capable of bi-directional communication with a communication module located external to the patient's body, the system comprising: (a) INS 10 and optionally the implantable drug pump; (b) the communication module; (c) a mobile telephone or similar device operably connected to the communication module and capable of receiving information therefrom or relaying information thereto; (e) a remote computer system, and (f) a communication system capable of bidirectional communication.

The preceding specific embodiments are illustrative of the practice of the invention. It is to be understood, therefore, that other expedients known to those skilled in the art or disclosed herein may be employed without departing from the invention or the scope of the appended claims.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination. All printed publications and patents referenced hereinabove are hereby incorporated by referenced herein, each in its respective entirety.

We claim:

1. A method for treating at least one of urinary voiding dysfunction, fecal voiding dysfunction, constipation, incontinence, urge frequency disorder, urinary retention disorder, sexual dysfunction, orgasmic dysfunction, erectile dysfunction, pelvic pain, prostatitis, prostatalgia and prostatodynia in a patient, comprising:

implanting a distal end of a first implantable medical electrical lead in tissue of the patient adjacent, around or in one of the bladder or portions thereof, the vagina or portions thereof, scrotal nerves or branches or portions thereof, the scrotum or portions thereof, sacro-tuberous ligament or branches or portions thereof, greater sciatic foramen or branches or portions thereof, or lesser sciatic foramen or branches or portions thereof, wherein the first lead comprises at least a first electrode;

operably connecting a proximal end of the at least first lead to an hermetically sealed implantable electrical pulse generator configured to provide at least one electrical stimulation pulse regime via at least the first lead;

implanting the implantable pulse generator within the patient; and delivering electrical stimulation pulses from the implantable pulse generator to one of the bladder or portions thereof, the vagina or portions thereof, scrotal nerves or branches or portions thereof, the scrotum or portions thereof, sacro-tuberous ligament or branches or portions thereof, greater sciatic foramen or branches or portions thereof, or lesser sciatic foramen or branches or portions thereof through the at least first lead and electrode, the pulses being provided in accordance with the electrical stimulation pulse regime and delivered in a configuration effective to provide at least partial relief from at least one of urinary voiding dysfunction, fecal voiding dysfunction, constipation, incontinence, urge frequency disorder, urinary retention disorder, sexual dysfunction, orgasmic dysfunction, erectile dysfunction, pelvic pain, prostatitis, prostatalgia and prostatodynia.

2. The method of claim 1, wherein the at least first lead comprises a beam steering lead comprising multiple electrodes.

3. The method of claim 1, wherein the at least first lead comprise an active fixation device or member disposed thereon, attached thereto or forming a portion thereof.

4. The method of claim 1, wherein the at least first lead includes a fixation device or member selected from the group consisting of a suture sleeve, a barb, a helical screw, a hook and a tissue in-growth mechanism.

5. The method of claim 1, further comprising providing, implanting, operably connecting and delivering electrical stimuli from a second implantable medical electrical lead, wherein the second lead comprises proximal and distal ends and at least one electrode.

6. The method of claim 5, further comprising delivering the electrical pulses through tissue disposed between the electrodes located on the first and second leads.

7. The method of claim 1, wherein the electrical stimulation pulses that are delivered to one of the bladder or portions thereof, the vagina or portions thereof, scrotal nerves or branches or portions thereof, the scrotum or portions thereof, sacro-tuberous ligament or branches or portions thereof, greater sciatic foramen or branches or portions thereof, or lesser sciatic foramen or branches or portions thereof cause paresthesia, or the masking or blocking pain signals originating in or carried by a desired or target nerve or nerve portion located in the vicinity of the at least one electrode.

8. The method of claim 1, further comprising providing a lead extension, operably connecting same between the proximal end of the at least first lead and the implantable pulse generator, and delivering the electrical stimulation pulses through the lead extension.

9. The method of claim 1, wherein the first lead comprises at least one electrode selected from the group consisting of an electrode formed from a portion of wire, a barb or a hook, a spherically-shaped electrode, and a helically-shaped electrode.

10. The method of claim 1, wherein the distance between the proximal and distal ends of the at least first lead is selected from the group consisting of about 6 inches, about 8 inches, about 10 inches, about 12 inches, about 14 inches, about 16 inches about 18 inches, about 20 inches and more than about 20 inches.

11. The method of claim 1, wherein the implantable pulse generator and the at least first lead are capable of generating and delivering electrical pulses having frequencies ranging between about 50 Hz and about 100 Hz, between about 10 Hz and about 250 Hz, or between about 0.5 Hz and about 500 Hz.

12. The method of claim 1, wherein the implantable pulse generator and the at least first lead are capable of generating and delivering electrical pulses having amplitudes ranging between about 1 Volt and about 10 Volts, between about 0.5 Volts and about 20 Volts, or between about 0.1 Volts and about 50 Volts.

13. The method of claim 1, wherein the implantable pulse generator and the at least first lead are capable of generating and delivering electrical pulses having pulse widths ranging between about 180 microseconds and about 450 microseconds, between about 100 microseconds and about 1000 microseconds, or between about 10 microseconds and about 5000 microseconds.

14. The method of claim 1, wherein delivering first electrical stimulation pulses comprises:
generating a plurality of different electrical signals, electrical pulses of the electrical signals having respective spatial or temporal phases for respective delivery to the first lead and at least a second lead; and
delivering the pulses to one of the bladder or portions thereof, the vagina or portions thereof, scrotal nerves or branches or portions thereof, the scrotum or portions thereof, sacro-tuberous ligament or branches or portions thereof, greater sciatic foramen or branches or portions thereof, or lesser sciatic foramen or branches or portions thereof.

15. The method of claim 1, wherein the electrical stimulation pulse regime provided to the patient is effective in providing at least one of urinary urgency relief or urinary frequency relief.

16. The method of claim 1, wherein the electrical stimulation pulse regime provided to the patient is effective in providing relief from sexual dysfunction.

17. The method of claim 1, further comprising concomitantly delivering a drug to the patient mid delivering the electrical stimulation regime.

18. The method of claim 17, further comprising providing, implanting and activating an implantable drug pump for providing the drug to the patient.

19. A method for treating urinary retention disorder in a patient comprising:
implanting a distal end of a first implantable medical electrical lead in tissue of the patient adjacent, around or in one of the pudendal nerve or branches or portions thereof, the prostatic plexus nerve or branches or portions thereof, the sacral splanchnic nerve or branches or portions thereof, the pelvic splanchnic nerve or branches or portions thereof, the prostate or branches or portions thereof, the pelvic floor, the colon or branches or portions thereof, the bladder or portions thereof, the vagina or portions thereof, the anus or portions thereof, the external anal sphincter or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Carnal or branches or portions thereof, sacro-tuberous ligament or branches or portions thereof, ischial tuberosity or branches or portions thereof, greater sciatic foremen or branches or portions thereof, or lesser sciatic foramen or branches or portions thereof, wherein the first lead comprises at least a first electrode;

operably connecting a proximal end of the at least first lead to an hermetically sealed implantable electrical pulse generator configured to provide at least one electrical stimulation pulse regime via at least the first lead;

implanting the implantable pulse generator within the patient; and delivering electrical stimulation pulses from the implantable pulse generator to one of the pudendal nerve or branches or portions thereof, the prostatic plexus nerve or branches or portions thereof, the sacral splanchnic nerve or branches or portions thereof, the pelvic splanchnic nerve or branches or portions thereof, the prostate or branches or portions thereof, the pelvic floor, the colon or branches or portions thereof, the bladder or portions thereof, the vagina or portions thereof, the anus or portions thereof, the external anal sphincter or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portion thereof, or lesser sciatic foramen or branches or portions thereof through the at least first lead and electrode, the pulses being provided in accordance with the electrical stimulation pulse regime and delivered in a configuration effective to provide at least partial relief from urinary retention disorder.

20. The method of claim 19,
wherein implanting the first lead comprises implanting the first lead in tissue of the patient adjacent, around or in one of the pudendal nerve or branches or portions thereof.

21. A method for treating at least one of prostatitis, prostatalgia or prostatodynia in a patient, comprising:
implanting a distal end of a first implantable medical electrical lead in tissue of the patient adjacent, around or in one of the colon or branches or portions thereof, the bladder or portions thereof, the vagina or portions thereof, the anus or portions thereof, the external anal sphincter or portions thereof, the urethra or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portions thereof, or lesser sciatic foramen or branches or portions thereof, wherein the first lead comprises at least a first electrode;

operably connecting a proximal end of the at least first lead to an hermetically sealed implantable electrical pulse generator configured to provide at least one electrical stimulation pulse regime via at least the first lead;

implanting the implantable pulse generator within the patient; and delivering electrical stimulation pulses front the implantable pulse generator to one of the colon or branches or portions thereof, the bladder or portions thereof, the vagina or portions thereof, the anus or portions thereof, the external anal sphincter or portions thereof, the urethra or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portions thereof, or lesser sciatic foramen or branches or portions thereof through the at least first lead and electrode, the pulses being provided in accordance with the electrical stimulation pulse regime and delivered in a configuration effective to provide at least partial relief from at least one of prostatitis, prostatalgia or prostatodynia, wherein the electrical stimulation pulses that are delivered to one of the colon or branches or portions thereof, the bladder or portions thereof, the vagina or portions thereof, the anus or portions thereof, the external anal sphincter or portions thereof, the urethra or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portions thereof, or lesser sciatic foramen or branches or portions thereof cause paresthesia, or the masking or blocking pain signals originating in or carried by a desired or target nerve or nerve portion located in the vicinity of the at least one electrode.

22. The method of claim 21, wherein implanting the first lead comprises:

delivering stimulation to a plurality of locations via a St. Mark's electrode, the locations comprising cue or more of the bladder or portions thereof, the vagina or portions thereof, scrotal nerves or branches or portions thereof, the scrotum or portions thereof, sacro-tuberous ligament or branches or portions thereof, greater sciatic foremen or branches or portions thereof, or lesser sciatic foremen or branches or portions thereof;

sensing an evoked response for each of the locations;

selecting one of the locations based on the evoked responses; and implanting electrodes of the first lead adjacent, around, or in tissue at the selected location.

23. The method of claim 22, wherein sensing an evoked response comprises sensing an anal or vaginal electromyogram for each of the locations.

24. The method of claim 23, further comprising determining a latency of the electromyogram for each location, wherein selecting one of the locations comprises selecting the location based on the latency.

25. A method for treating at least one of urinary voiding dysfunction, fecal voiding dysfunction, constipation, incontinence, urge frequency disorder, urinary retention disorder, sexual dysfunction, orgasmic dysfunction, erectile dysfunction, pelvic pain, prostatitis, prostatalgia and prostatodynia in a patient, comprising:

delivering stimulation to a plurality of locations via a St. Mark's electrode, the locations comprising one or more of the sacral nerve or branches or portions thereof, the pudendal nerve or branches or portions thereof, the hypogastric nerve or branches or portions thereof, the prostatic plexus nerve or branches or portions thereof, the sacral splanchnic nerve or branches or portions thereof, the pelvic splanchnic nerve or branches or portions thereof, the prostate or branches or portions thereof, the pelvic floor, the colon or branches or portions thereof, the bladder or portions thereof, the vagina or portions thereof, the anus or portions thereof, the external anal sphincter or portions thereof, the urethra or portions thereof, the penile dorsal nerve or portions thereof, inferior rectal nerves or branches or portions thereof, perineal nerves or branches or portions thereof, scrotal nerves or branches or portions thereof, the scrotum or portions thereof, Alcock's Canal or branches or portions thereof, sacro-tuberous ligament or branches or portions thereof, ischial tuberosity or branches or portions thereof, greater sciatic foramen or branches or portions thereof, or lesser sciatic foramen or branches or portions thereof;

sensing an evoked response for each of the locations;

selecting one of the locations based on the evoked responses;

implanting electrodes of the first implantable medical electrical lead in tissue of the patient adjacent, around or in the selected location; and delivering electrical stimulation pulses from an implantable electrical pulse generator to at least a portion of the tissue of the patient through the at least first lead and electrode, the pulses being provided in accordance with the electrical stimulation pulse regime and providing to the patient at least partial relief from at least one of urinary voiding dysfunction, fecal voiding dysfunction, constipation, incontinence, urge frequency disorder, urinary retention disorder, sexual dysfunction, orgasmic dysfunction, erectile dysfunction, pelvic pain, prostatitis, prostatalgia and prostatodynia.

26. The method of claim 25, wherein sensing an evoked response comprises sensing an anal or vaginal electromyogram for each of the locations.

27. The method of claim 26, further comprising determining a latency of the electromyogram for each location, wherein selecting one of the locations comprises selecting the location based on the latency.

28. A method for treating pelvic pain comprising:

implanting a distal end of at least a first medical electrical lead in tissue of the patient adjacent, around or in at least one of the colon or branches or portions thereof, the bladder or portions thereof, the vagina or portions thereof, the anus or portions thereof, the external anal sphincter or portions thereof, the urethra or portions thereof, inferior rectal nerves or branches or portions thereof, perineal nerves or branches or portions thereof, scrotal nerves or branches or portions thereof, the scrotum or portions thereof, or the sacro-tuberous ligament or branches or portions thereof, wherein the first lead comprises at least a first electrode;

operably connecting a proximal end of the at least first lead to an hermetically sealed implantable electrical pulse generator configured to provide at least one electrical stimulation pulse regime via at least the first lead;

implanting the implantable pulse generator within the patient; and delivering electrical stimulation pulses from the implantable pulse generator to at least one of the colon or branches or portions thereof, the bladder or portions thereof, the vagina or portions thereof, the anus or portions thereof, the external anal sphincter or portions thereof, the urethra or portions thereof, inferior rectal nerves or branches or portions thereof, perineal nerves or branches or portions thereof, scrotal nerves or branches or portions thereof, the scrotum or portions thereof, or the sacro-tuberous ligament or branches or portions thereof through the at least first lead and electrode, the pulses being provided in accordance with the electrical stimulation pulse regime and in a configuration effective to provide the patient at least partial relief from pelvic pain, wherein the electrical stimulation pulses that are delivered to the desired nerve target sites or portions cause paresthesia, or the masking or blocking pain signals originating in or carried by a desired or target nerve or nerve portion located in the vicinity of the at least one electrode.

* * * * *

UNITED STATES PATENT AND TRADEMARK OFFICE
CERTIFICATE OF CORRECTION

PATENT NO. : 7,328,068 B2  Page 1 of 1
APPLICATION NO. : 10/723316
DATED : February 5, 2008
INVENTOR(S) : Michele Spinelli It is certified that error appears in the above-identified patent and that said Letters Patent is hereby corrected as shown below:

On the Title Page:
Item [74] "Shumaker & Sieffect, P.A." should read -- Shumaker & Sieffert --.

Column 21
Line 47, "patient mid delivering" should read -- patient and delivering --.

Column 23
Line 6, "pulses front the" should read -- pulses from the --.

Line 47, "comprising cue or" should read -- comprising one or --.

Signed and Sealed this

Nineteenth Day of August, 2008

JON W. DUDAS
*Director of the United States Patent and Trademark Office*